(12) United States Patent
Lee et al.

(10) Patent No.: US 10,319,465 B2
(45) Date of Patent: Jun. 11, 2019

(54) SYSTEMS AND METHODS FOR ALIGNING SEQUENCES TO GRAPH REFERENCES

(71) Applicant: Seven Bridges Genomics Inc., Cambridge, MA (US)

(72) Inventors: Wan-Ping Lee, Somerville, MA (US); Alyssa Dayan, Cambridge, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 36 days.

(21) Appl. No.: 15/353,105

(22) Filed: Nov. 16, 2016

(65) Prior Publication Data

US 2018/0137387 A1    May 17, 2018

(51) Int. Cl.
| | | |
|---|---|---|
| *G16B 45/00* | (2019.01) | |
| *G06K 9/00* | (2006.01) | |
| *G06K 9/68* | (2006.01) | |

(52) U.S. Cl.
CPC ......... *G16B 45/00* (2019.02); *G06K 9/00134* (2013.01); *G06K 9/00147* (2013.01); *G06K 9/6892* (2013.01); *G06K 2209/07* (2013.01)

(58) Field of Classification Search
None
See application file for complete search history.

(56) References Cited

U.S. PATENT DOCUMENTS

| | | |
|---|---|---|
| 5,511,158 A | 4/1996 | Sims |
| 5,701,256 A | 12/1997 | Marr et al. |
| 6,223,128 B1 | 4/2001 | Allex et al. |
| 7,577,554 B2 | 8/2009 | Lystad et al. |
| 7,580,918 B2 | 8/2009 | Chang et al. |
| 7,809,509 B2 | 10/2010 | Milosavljevic |
| 7,885,840 B2 | 2/2011 | Sadiq et al. |
| 7,917,302 B2 | 3/2011 | Rognes |
| 8,209,130 B1 | 6/2012 | Kennedy et al. |
| 8,340,914 B2 | 12/2012 | Gatewood et al. |
| 8,370,079 B2 | 2/2013 | Sorenson et al. |

(Continued)

FOREIGN PATENT DOCUMENTS

| | | |
|---|---|---|
| JP | 2005316605 A | * 11/2005 |
| WO | 2012098515 A1 | 7/2012 |

(Continued)

OTHER PUBLICATIONS

JP2005316605A [machine translation] (Year: 2005).*

(Continued)

*Primary Examiner* — Michelle M Entezari
(74) *Attorney, Agent, or Firm* — Kip L. Bodi

(57) ABSTRACT

Various embodiments of the disclosure relate to systems and methods for aligning a sequence read to a graph reference. In one embodiment, the method comprises selecting a first node from a graph reference, the graph reference comprising a plurality of nodes connected by a plurality of directed edges, at least one node of the plurality of nodes having a nucleotide sequence. The method further comprises traversing the graph reference according to a depth-first search, and comparing a sequence read to nucleotide sequences generated from the traversal of the graph reference. The traversal of the graph is then modified in response to a determination that each and every node associated with a given nucleotide sequence was previously evaluated.

23 Claims, 11 Drawing Sheets

(56) References Cited

U.S. PATENT DOCUMENTS

| | | | |
|---|---|---|---|
| 8,478,543 B2* | 7/2013 | Pierce | G16B 15/00 702/19 |
| 8,639,847 B2 | 1/2014 | Blaszczak et al. | |
| 9,063,914 B2 | 6/2015 | Kural et al. | |
| 9,092,402 B2 | 7/2015 | Kural et al. | |
| 9,116,866 B2 | 8/2015 | Kural | |
| 9,390,226 B2 | 7/2016 | Kural | |
| 9,817,944 B2 | 11/2017 | Kural | |
| 2005/0089906 A1 | 4/2005 | Furuta et al. | |
| 2005/0159898 A1* | 7/2005 | Yasuda | G16B 30/00 702/20 |
| 2007/0166707 A1* | 7/2007 | Schadt | C12Q 1/6827 435/6.11 |
| 2008/0077607 A1 | 3/2008 | Gatawood et al. | |
| 2008/0294403 A1 | 11/2008 | Zhu et al. | |
| 2009/0119313 A1 | 5/2009 | Pearce | |
| 2009/0300781 A1 | 12/2009 | Bancroft et al. | |
| 2009/0318310 A1 | 12/2009 | Liu et al. | |
| 2010/0169026 A1 | 7/2010 | Sorenson et al. | |
| 2011/0004413 A1 | 1/2011 | Carnevali et al. | |
| 2011/0098193 A1 | 4/2011 | Kingsmore et al. | |
| 2011/0280907 A1* | 11/2011 | Mchardy | A61K 39/145 424/209.1 |
| 2012/0041727 A1 | 2/2012 | Mishra et al. | |
| 2012/0239706 A1 | 9/2012 | Steinfadt | |
| 2012/0330566 A1 | 12/2012 | Chaisson | |
| 2013/0059740 A1 | 3/2013 | Drmanac et al. | |
| 2013/0073214 A1 | 3/2013 | Hyland et al. | |
| 2013/0124100 A1 | 5/2013 | Drmanac et al. | |
| 2013/0311106 A1 | 11/2013 | White et al. | |
| 2014/0025312 A1 | 1/2014 | Chin et al. | |
| 2014/0051588 A9 | 2/2014 | Drmanac et al. | |
| 2014/0136120 A1 | 5/2014 | Colwell et al. | |
| 2014/0200147 A1 | 7/2014 | Bartha et al. | |
| 2014/0278590 A1 | 9/2014 | Abbassi et al. | |
| 2014/0280360 A1 | 9/2014 | Webber et al. | |
| 2014/0323320 A1 | 10/2014 | Jia et al. | |
| 2015/0056613 A1 | 2/2015 | Kural | |
| 2015/0057946 A1 | 2/2015 | Kural | |
| 2015/0110754 A1 | 4/2015 | Bai et al. | |
| 2015/0112602 A1 | 4/2015 | Kural et al. | |
| 2015/0112658 A1 | 4/2015 | Kural et al. | |
| 2015/0197815 A1 | 7/2015 | Kural | |
| 2015/0199472 A1 | 7/2015 | Kural | |
| 2015/0199473 A1 | 7/2015 | Kural | |
| 2015/0199474 A1 | 7/2015 | Kural | |
| 2015/0199475 A1 | 7/2015 | Kural | |
| 2015/0227685 A1 | 8/2015 | Kural | |
| 2015/0293994 A1 | 10/2015 | Kelly | |
| 2015/0302145 A1 | 10/2015 | Kural et al. | |
| 2015/0310165 A1* | 10/2015 | Mann | G16B 30/00 506/2 |
| 2015/0310167 A1 | 10/2015 | Kural et al. | |
| 2015/0344970 A1 | 12/2015 | Vogelstein et al. | |
| 2015/0347678 A1 | 12/2015 | Kural | |
| 2015/0356147 A1* | 12/2015 | Mishra | G06F 16/24575 707/693 |
| 2016/0259880 A1 | 9/2016 | Semenyuk | |
| 2016/0306921 A1 | 10/2016 | Kural | |
| 2016/0364523 A1 | 12/2016 | Locke et al. | |
| 2017/0058325 A1 | 3/2017 | Locke et al. | |
| 2017/0058341 A1 | 3/2017 | Locke et al. | |
| 2017/0058365 A1 | 3/2017 | Locke et al. | |
| 2017/0198351 A1 | 7/2017 | Lee et al. | |
| 2017/0199959 A1 | 7/2017 | Locke | |
| 2017/0199960 A1 | 7/2017 | Ghose et al. | |
| 2017/0242958 A1 | 8/2017 | Brown | |
| 2017/0316353 A1* | 11/2017 | Frewen | G06Q 10/0633 |

FOREIGN PATENT DOCUMENTS

| | | |
|---|---|---|
| WO | 2012142531 A2 | 10/2012 |
| WO | 2015027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Simpson, Jared T., Kim Wong, Shaun D. Jackman, Jacqueline E. Schein, Steven JM Jones, and Inanç Birol. "ABySS: a parallel assembler for short read sequence data." Genome research 19, No. 6 (2009): 1117-1123. (Year: 2009).*

Agarwal, 2013, SINNET: Social Interaction Network Extractor from Text, Proc IJCNLP 33-36.

Aguiar, 2012, HapCompass: A fast cycle basis algorithm for accurate haplotype assembly of sequence data, J Comp Biol 19(6):577-590.

Aguiar, 2013, Haplotype assembly in polyploid genomes and identical by descent shared tracts, BioInformatics 29(13): i352-i360.

Airoldi, 2008, Mixed membership stochastic blockmodels, JMLR 9:1981-2014.

Albers, 2011, Dindel: Accurate indel calls from short-read data, Genome Research 21:961-973.

Altera, 2007, Implementation of the Smith-Waterman algorithm on reconfigurable supercomputing platform, White Paper ver 1.0 (18 pages).

Altschul, 1986, Optimal Sequence Alignment Using Affine Gap Costs, Bull Math Biol 48(5/6):603-616.

Bansal, 2008, An MCMC algorithm for haplotype assembly from whole-genome sequence data, Genome Res 18:1336-1346.

Bao, 2013, BRANCH: boosting RNA-Seq assemblies with partial or related genomic sequences, Bioninformatics 29 (10):1250-1259.

Barbieri, 2013, Exome sequencing identifies recurrent SPOP, FOXA1 and MED12 mutations in prostate cancer, Nature Genetics 44:6 685-689.

Beerenwinkel, 2007, Conjunctive Bayesian Networks, Bernoulli 13(4), 893-909.

Berlin, 2014, Assembling large genomes with single-molecule sequencing and locality sensitive hashing, bioRxiv preprint (35 pages); retrieved from the internet on Jan. 29, 2015, at.

Bertrand, 2009, Genetic map refinement using a comparative genomic approach, J Comp Biol 16(10):1475-1486.

Black, 2005, A simple answer for a splicing conundrum. PNAS 102:4927-8.

Boyer, 1977, A Fast String Searching Algorithm, Comm ACM 20(10)162-772.

Browning et al, Haplotype phasing: existing methods and new developments, 2011, vol. 12, Nature Reviews Genetics.

Caboche et al, Comparison of mapping algorithms used in high-throughput sequencing: application to Ion Torrent data, 2014, vol. 15, BMC Genomics.

Cartwright, DNA assembly with gaps (DAWG): simulating sequence evolution, 2005, pp. iii31-iii38, vol. 21, Oxford University Press.

Chang, 2005, The application of alternative splicing graphs in quantitative analysis of alternative splicing form from EST database, Int J Comp Appl Tech 22(1):14.

Chin, 2013, Nonhybrid finished microbial genome assemblies from long-read SMRT sequencing data, Nat Meth 10(6):563-569.

Chuang, 2001, Gene recognition based on DAG shortest paths, Bioinformatics 17(Suppl. 1):556-s64.

Compeau, 2011, How to apply de Bruijn graphs to genome assembly, Nat Biotech 29(11):987-991.

DePristo, 2011, A framework for variation discovery and genotyping using next-generation DNA sequencing data, Nat Gen 43:491-498.

(56) References Cited

OTHER PUBLICATIONS

Duan et al., Optimizing de novo common wheat transcriptome assembly using short-read RNA-Seq data. (2012) pp. 1-12, vol. 13, BMC Genomics.
Dudley, 2009, A quick guide for developing effective bioinformatics programming skills, PLoS Cornput Biol 5(12): e1000589.
Durbin, 2014, Efficient haplotype matching and storage using the positional Burrows-Wheeler transform (PBWT), Bioinformatics 30(9):1266-1272.
Endelman, 2011, New algorithm improves fine structure of the barley consensus SSNP map, BMC Genomics 12(1):407 (and whole document).
Exam Report issued in EP14803268.3.
Extended European Search Report issued in EP 14837955.5.
Extended European Search Report issued in EP 14847490.1.
Extended European Search Report issued in EP 14854801.9.
Farrar, 2007, Striped Smith-Waterman speeds database searches six times over other SIMD implementations, Bioinformatics 23(2):156-161.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2013, Genome-guided transcriptome assembly in the age of next-generation sequencing, IEEE/ACM Trans Comp Biol Bioinf 10(5):1234-1240.
Garber, 2011, Computational methods for transcriptorne annotation and quantification using RNA-Seq, Nat Meth 8(6):469-477.
Gerlinger, 2012, Intratumor Heterogeneity and Branched Evolution Revealed by Multiregion Sequencing, 366:10 883-892.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Grasso, 2004, Combining partial order alignment and progressive multiple sequence alignment increases alignment speed and scalability to very large alignment problems. Bioinformatics 20(10):1546-1556.
Haas, 2004, DAGchainer: a tool for mining segmental genome duplications and synteny, Bioinformatics 20(18):3643-3646.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Homer, 2010, Improved variant discovery through local re-alignment of short-read next generation sequencing data using SRMA, Genome Biol 11(10):R99.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002.
International HapMap Censortium, 2005, A haplotype map of the human genome. Nature 437:1299-1320.
International Search Report and Written Opinion dated Aug. 31, 2017, for International Application No. PCT/US2017/018830 with International Filing Date Feb. 22, 2017, (11 pages).
International Search Report and Written Opinion dated Mar. 31, 2015 for International Application No. PCT/US2015/010604 filed Jan. 8, 2015 (13 pages).
International Search Report and Written Opinion dated Apr. 19, 2017 for International Patent Application No. PCT/US2017/012015, (14 Pages).
International Search Report and Written Opinion dated Feb. 17, 2015, for International Patent Application No. PCT/US2014/061156, filed Oct. 17, 2014 (19 pages).
International Search Report and Written Opinion dated Jan. 10, 2017, for International Patent Application No. PCT/US16/57324 with International Filing Date Oct. 17, 2016, (7 pages).
International Search Report and Written Opinion dated Mar. 19, 2015, for International Application No. PCT/US2014/061162 with International Filing Date Oct. 17, 2014, (12 pages).
International Search Report and Written Opinion dated May 5, 2016, for International Patent Application No. PCT/US2016/020899, wiht International Filing Date Mar. 4, 2016, (12 pages).
International Search Report and Written Opinion dated Nov. 17, 2015 for International Patent Application No. PCT/US2015/048891, (11 Pages).
International Search Report and Written Opinion dated Apr. 7, 2017, for International Patent Application No. PCT/US17/13329, filed Jan. 13, 2017, (9 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014, (22 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No, PCT/US2014/060690, filed Oct. 15, 2014, PCT/US2014/060690 (11 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201 with International Filing Date May 19, 2016, (14 pages).
International Search Report and Written Opinion dated Sep. 7, 2016, for International Application No. PCT/US2016/036873 with International filing date Jun. 10, 2016, (8 pages).
Kano, 2010, Text mining meets workflow: linking U-Compare with Taverna, Bioinformatics 26(19):2486-7.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Kumar, 2010, Comparing de novo assemblers for 454 transcriptome data, BMC Genomics 11:571.
Lam, 2008, Compressed indexing and local alignment of DNA, Bioinformatics 24(6):791-97.
Langrnead, 2009, Ultrafast and memory-efficient alignment of short DNA sequences to the human genome, Genome Biol 10:R25.
Larkin, 2007, Clustal W and Clustal X version 2.0, Bioinformatics 23(21):2947-2948.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.

(56) References Cited

OTHER PUBLICATIONS

Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, Accurate read mapping using a graph-based human pan-genome, ASHG 2014 Abstracts.
LeGault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29(18)2300-2310.
Leipzig, 2004, The alternative splicing gallery (ASG): Bridging the gap between genome and transcriptome, Nuc Acids Res 23(13):3977-3983.
Li, 2009, Fast and accurate short read alignment with Burrows-Wheeler Transform. Bioinformatics 25:1754-60.
Li, 2010, A survey of sequence alignment algorithms for next-generation sequencing, Briefings in Bionformatics 11(5):473-483.
Lipman, 1985, Rapid and sensitive protein similarity searches, Science 227(4693):1435-41.
Lucking, 2011, PICS-Ord: unlimited coding of ambiguous regions by pairwise identity and cost scores ordination, BMC Bioinf 12:10.
Ma, 2010, Multiple genome alignment based on longest path in directed acyclic graphs, Int J Bioinformatics 6(4):366-683.
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retrieved from the internet on Jun. 3, 2016, at.
Marth et al., 1999—A general approach to single-nucleotide polymorphism discovery, pp. 452-456, vol. 23, Nature Genetics.
Mazrouee, 2014, FastHap: fast and accurate single individual haplotype reconstructions using fuzzy conflict graphs, Bioinformatics 30:i371-i378.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Mount, 2001, Multiple Sequence Alignment, Bioinformatics, 2001, Cold Spring Harbor Laboratory Press, Cold Spring Harbor, New York, pp. 139-204.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Nagarajan, 2013, Sequence assembly demystified, Nat Rev 14:157-167.
Needleman, 1970, A general method applicable to the search for similarities in the amino acid sequence of two proteins, J Mol Biol 48(3):443-453.
Peixoto, 2014, Efficient Monte Carlo and greedy heuristic for the inference of stochastic block models, Phys. Rev. E 89, 012804.
Pruesse, 2012, SINA: Accurate high-throughput multiple sequence alignment of ribosomal RNA genes, Bioinformatics 28:14 1823-1829.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator. Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Sturgeon, RCDA: a highly sensitive and specific alternatively spliced transcript assembly tool featuring upstream consecutive exon structures, Genornics, Dec. 2012, 100(6): 357-362.
Subramanian, 2008, DIALIGN-TX: greedy and progessive approaches for segment-based multiple sequence alignment, Alg Mol Biol 3(1):1-11.
Sun, 2006, Pairwise Comparison Between Genomic Sequences and Optical maps, dissertation, New York University (131 pages); retreived from the internet on Jun. 3, 2016, at.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tarhio, 1993, Approximate Boyer-Moore String Matching, SIAM J Comput 22(2):243-260.
Thomas, 2014, Community-wide effort aims to better represent variation in human reference genome, Genome Web (11 pages).
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Written Opinion issued in SG 11201601124Y.
Written Opinion issued in SG 11201602903X.
Written Opinion issued in SG 11201603039P.
Written Opinion issued in SG 11201603044S.
Written Opinion issued in SG 11201605506Q.
Wu, 2010, Fast and SNP-tolerant detection of complex variants and splicing in short reads, Bioinformatics, 26 (7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yanovsky, 2008, Read mapping algorithms for single molecule sequencing data, Proc 8th Int Workshop Alg Bioinformatics 5251:38-49.

(56) References Cited

OTHER PUBLICATIONS

Yu, 2010, The construction of a tetraploid cotton genome wide comprehensive reference map, Genomics 95:230-240.
Zeng, 2013, PyroHMMvar: a sensitive and accurate method to call short indels and SNPs for Ion Torrent and 454 data, Bioinformatics 29:22 2859-2868.
Zhang et al.. Construction of a high-density genetic map for sesame based on large scale marker development by specific length amplified fragment (SLAF) sequencing. (2013) pp. 1-12, vol. 13, BMC Plant Biology.

* cited by examiner

SYSTEMS AND METHODS FOR ALIGNING SEQUENCES TO GRAPH REFERENCES

FIELD OF THE DISCLOSURE

The present disclosure generally relates to bioinformatics.

BACKGROUND

The completion of the first human reference genome enabled the discovery of the whole catalogue of human genes, ushering in a new era of genomics research to discover the molecular basis of disease. One approach for genomic analyses relies on reference-guided alignment, the accurate mapping of relatively short sequence reads generated by Next Generation Sequencing (NGS) technologies to a reference genome. Reference-guided alignment has led to the development of new alignment and variant identification algorithms suited for these new high-throughput technologies, with an emphasis on speed and efficiency.

Alignment algorithms for reference-guided alignment seek to identify the most likely position on a reference genome from which a particular sequence read originated. To that end, alignment algorithms will allow some deviation in nucleotide sequence from the reference at a mapped position to allow for both unknown variation and error in the sequence read. However, this strategy leads to a phenomenon known as "reference bias," in which the algorithm may force placement, and in so doing misalign, sequence reads against the reference. Further, sequence reads from a sample having regions of low homology with the reference genome may result in a high percentage of unaligned reads. These factors lead to low discovery and concordance rates for high complexity variants, such as short insertions and deletions ("indels"), inversions, duplications, tandem repeats, and mobile element insertions.

Accounting for variations within the reference itself can solve these issues to some extent. For example, sequence reads may be aligned against a reference sequence construct that accounts for one or more variants, which may be referred to as a graph reference sequence construct, or simply a graph reference. In contrast to a linear reference sequence, a graph reference can incorporate myriad types of information about genomic variations, minimizing the effects of reference bias. In a graph reference, variations may be represented by a respective path through the graph underlying the graph reference. Thus, known variations can be reliably accounted for and identified by aligning reads containing the known variation to a sequence path that includes that variation. This aids the accurate placement of sequence reads, and further allows for variations in a sample to be identified simply by noting the primary path on which the majority of sequence reads lie. Further, this improved alignment allows for more unknown variations to be discovered than by traditional means.

However, as the number of variants in a graph reference increases, the number of paths through the graph that must be evaluated during alignment also increases. In complex or dense regions of the graph, this can lead to a combinatorial explosion, rendering sequence read alignment computationally intractable. One approach to solving this problem is to reduce the number of variants represented by a graph, but this results in a loss of sensitivity. Accordingly, there is a need for improvements in aligning sequence reads to graph references.

SUMMARY

Aligning sequence reads against a graph reference that accounts for genomic variations aids accurate placement of sequence reads and facilitates the identification of variants based on the results of the alignment. However, the inventors have recognized and appreciated that conventional techniques for aligning sequence reads against graph references may be improved upon because they are computationally expensive due to the complexity of the underlying graphs. Thus, the inventors have recognized that the problem of aligning sequence reads to complex graph references is solved by a graph traversal that reduces the number of paths for consideration based on a status of previously considered regions of the graph. Regions of the graph are excluded from consideration when a combination of nodes currently being considered for comparison to a sequence read are known to have been previously evaluated during a previous traversal. Further, the inventors have recognized that aligning short subsequences, or k-mers, of a sequence read to a graph reference using such a graph traversal is particularly efficient as it further reduces the number of paths that must be considered. The aligned locations of these k-mers are then extended to identify a full position for alignment. These features, individually and in combination, result in extremely efficient systems and methods of sequence read alignment, presenting a substantial improvement in the field of sequence alignment and assembly, improving the speed of graph-based reference alignment, and leading to further advances in genomics, next-generation sequencing, personalized medicine, and related fields.

In one embodiment, a system for aligning a sequence read to a graph reference comprises at least one computer hardware processor and at least one non-transitory computer-readable storage medium. The computer-readable storage medium stores a plurality of sequence reads and a graph reference comprising a plurality of nodes connected by a plurality of edges, wherein at least one node of the plurality of nodes has an associated nucleotide sequence. The storage medium further stores processor-executable instructions that, when executed by the at least one computer hardware processor, cause the at least one computer hardware processor to select a first node of the plurality of nodes and identify a first path by traversing the graph reference. The first path starts from the first node and comprises at least one child node of the first node, and the at least one first nucleotide sequence generated from the first path is then compared with the sequence read. A second path is then identified by traversing the graph reference, wherein the second path starts from the first node and comprises at least one node not considered by the first path. At least one second nucleotide sequence generated from the second path is then compared with the sequence read. Further, this comparison comprises determining whether the at least one second nucleotide sequence generated from the second path has not been previously generated by the first path. A best-fit position of the sequence read is identified on the graph reference; the best-fit position is reported as the aligned position.

In some embodiments, traversing the graph reference can comprise performing a depth-first search. In certain embodiments, a path can comprise one or more nodes. In certain embodiments, identifying a first path by traversing the graph reference comprises following outgoing edges of successive nodes until reaching a last node having no outgoing edges. In these embodiments, identifying a second path by traversing the graph reference can comprise backtracking from the last node having no outgoing edges. Additionally, backtracking from the last node having no outgoing edges can further comprise identifying a node having a previously unfollowed outgoing edge, following the previously unfollowed outgoing edge, and following outgoing edges of successive nodes until reaching a last node having no outgoing edges.

In some embodiments, each node can further comprise a followed indicator that indicates which of its outgoing directed edges have been traversed. In these embodiments, traversing the graph reference further comprises updating the followed indicator when following an outgoing edge from that node. In further embodiments, each node further comprises a visited indicator that indicates whether all of its outgoing directed edges have been traversed. In these embodiments, traversing the graph reference can further comprise determining whether a node's followed indicator indicates that all of its outgoing directed edges have been traversed, and updating the node's visited indicator to indicate that all of the outgoing directed edges have been traversed. The node's followed indicator is then reset to indicate that all of the outgoing directed edges have not been traversed, and the traversal then backtracks from that node. In certain embodiments, comparing at least one second nucleotide sequence generated from the second path with the sequence read further can comprise considering whether the at least one second nucleotide sequence is generated entirely from nodes having visited indicators that indicate all of the outgoing directed edges of those nodes have been traversed.

In some embodiments, comparing at least one first nucleotide sequence generated from the first path with the sequence read can comprise concatenating nucleotide sequences associated with the nodes in the first path into a concatenated nucleotide sequence, identifying a first set of substrings of the first concatenated nucleotide sequence, and comparing the first set of substrings to the sequence read. In these embodiments, comparing at least one second nucleotide sequence generated from the second path with the sequence read can comprise concatenating nucleotide sequences associated with the nodes in the second path into a second concatenated nucleotide sequence, identifying a second set of substrings of the second concatenated nucleotide sequence, and comparing each substring of the second set of substrings to the sequence read if and only if a substring is not within the first set of substrings. In further embodiments, comparing each substring of the second set of substrings to the sequence read if and only if a substring is not within the first set of substrings can comprise considering whether a substring is generated from at least one node that was not present in the first path. In these embodiments, each node can further comprise a visited indicator that indicates whether all of that node's outgoing directed edges have been traversed. In such embodiments, comparing each substring of the second set of substrings can further comprises determining whether each of the nodes associated with a substring have visited indicators that indicate all of the outgoing directed edges of those nodes have been traversed. If each of the nodes associated with the substring have visited indicators that indicate all of the outgoing directed edges of those nodes have been traversed, then the most recently added node from the second path is removed and it is considered whether any remaining nodes in the second path have an unfollowed outgoing edge. However, if any of the nodes associated with the substring have visited indicators that indicate all of the outgoing directed edges of those nodes have not been traversed, the substring is compared with the sequence read. In these embodiments, comparing the substring with the sequence read can further comprise generating the substring from those nodes.

In some embodiments, identifying a second path by traversing the graph reference can comprise identifying a quantity of nodes within the graph reference, traversing a portion of the graph reference, and modifying traversal of the graph in response to a determination that a region of the graph has been previously considered by the first path. In other embodiments, identifying a first path by traversing the graph reference can comprises considering whether the first node has an unfollowed child node, and if the first node has an unfollowed child node, adding the unfollowed child node to the first path.

In some embodiments, the sequence read can comprise a k-mer of the sequence read. In these embodiments, comparing nucleotide sequences generated from a path with the sequence read can comprise comparing a k-mer of the sequence read with the nucleotide sequences. In these embodiments, the k-mer can begin from the first base of the sequence read, and the length of the k-mer can be between 5 and 30 base pairs. Further, in certain embodiments, the one or more best-fit positions of the k-mer of the sequence read can be determined. In these embodiments, a best-fit position of the sequence read is determined by considering additional nucleotides adjacent to the best-fit positions of the k-mer of the sequence read.

In some embodiments, determining a best-fit position of the sequence read on the graph reference can further comprise aligning the sequence read to the graph reference using a second alignment algorithm. In these embodiments, the second alignment algorithm can be selected from the group consisting of: the Smith-Waterman algorithm and a graph-aware Smith-Waterman algorithm.

In another embodiment, a method for aligning a sequence read to a graph reference can comprise selecting a first node from a graph reference. The graph reference comprises a plurality of nodes connected by a plurality of directed edges, wherein at least one node of the plurality of nodes has a nucleotide sequence. The method can further comprise traversing the graph reference according to a depth-first search, and comparing a sequence read to nucleotide sequences generated from the traversal of the graph reference. Traversal of the graph reference is modified in response to a determination that each and every node associated with a given nucleotide sequence was previously evaluated.

In some embodiments, traversing the graph reference according to a depth-first search comprises adding nodes to a search path, wherein the nodes are ordered in the search path according to their directed edges. In these embodiments, modifying traversal of the graph reference in response to a determination that each and every node associated with a given nucleotide sequence was previously evaluated comprises removing those nodes from the search path. Further, in certain embodiments, every node may be added to the search path at least once. In certain embodiments, comparing a sequence read to nucleotide sequences generated from the traversal of the graph reference can comprise generating nucleotide sequences by concatenating the nucleotide sequences associated with each node in the search path according to the directionality of a set of edges associated with the search path.

In some embodiments, comparing a sequence read to nucleotide sequences generated from the traversal of the graph reference further can further comprise applying a string matching algorithm that provides a shift value. In these embodiments, the string matching algorithm can be the Tarhio-Ukkonen algorithm. Additionally, in some embodiments, the graph reference can represent a region of a reference genome between 50 and 500 base pairs.

In another embodiment, a system for aligning a sequence read to a graph reference comprises at least one computer hardware processor and at least one non-transitory computer-readable storage medium. The storage medium stores a graph reference and processor-executable instructions that, when executed by the at least one computer hardware processor, cause the at least one computer hardware processor to create a search path according to a depth-first search. The search path can comprise one or more nodes of the graph reference that are connected by one or more directed edges. The depth-first search can comprise extending the search path by adding an unfollowed child node of the most recently added node to the search path and removing the most recently added node when the most recently added node has no unfollowed child nodes. Nucleotide sequences are then generated for comparison with the sequence read by concatenating nucleotide sequences associated with the one or more nodes in the search path. It is then determined whether a nucleotide sequence of the set of nucleotide sequences is generated entirely from nodes that have previously been considered by the depth-first search. In response to the determination, the depth-first search can be modified by removing the most recently added node from the search path.

BRIEF DESCRIPTION OF THE DRAWINGS

FIGS. 1 through 11, wherein like parts are designated by like reference numerals throughout, illustrate an example embodiment of a system and method for the implementation of a sequence variation graph alignment system. Although the present disclosure describes the system and method with reference to the example embodiments described in the figures, it should be understood that many alternative forms can embody the present disclosure. One of ordinary skill in the art will additionally appreciate different ways to alter the parameters of the embodiments disclosed in a manner still in keeping with the spirit and scope of the present disclosure.

FIG. 1 is a block diagram illustrating a graph alignment system in accordance with some embodiments of the technology described herein;

FIG. 2 is an illustrative diagram of a graph-based reference sequence construct in accordance with some embodiments of the technology described herein;

FIG. 3 is a block diagram illustrating a graph alignment engine in accordance with some embodiments of the technology described herein;

FIG. 4 is a flow diagram illustrating a method of aligning a sequence read to a graph reference in accordance with some embodiments of the technology described herein;

FIG. 5 is a flow diagram illustrating a method of aligning a sequence read to a graph reference according to a depth-first search in accordance with some embodiments of the technology described herein;

DETAILED DESCRIPTION

Figure 1:
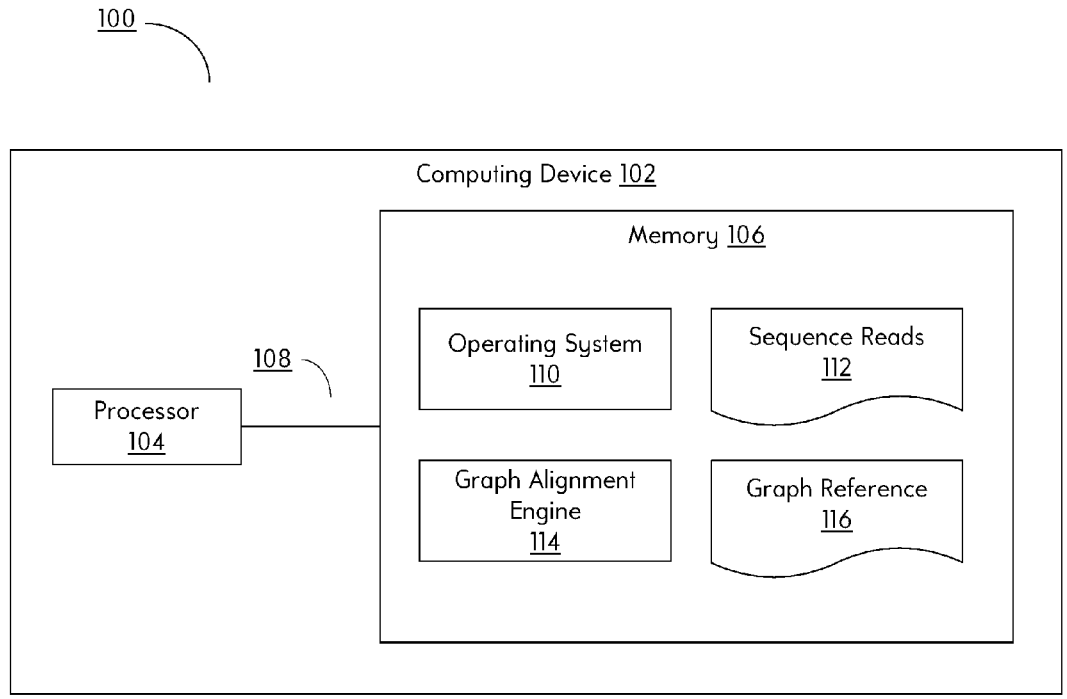

Embodiments of the disclosure describe a novel method for sequence read alignment against a graph reference that significantly increases the efficiency and speed of sequence read alignment in dense regions of the graph by reducing the number of paths for consideration. Aligning sequence reads against a graph reference, which accounts for known genomic variations, aids accurate placement of sequence reads and facilitates identification of variants based on results of the alignment. However, the inventors have recognized and appreciated that conventional techniques for aligning sequence reads against graph references may be improved upon because they are computationally expensive and may produce inaccurate results due to the complexity of the underlying graphs. Since a variant in a graph reference may be represented by a respective path through the graph underlying the graph reference, increasing the number of variants increases the number of paths that must be evaluated during alignment of sequence reads to the graph reference. This in turn increases the computational complexity of performing the alignment.

Our knowledge of the diversity of the human genome, and other genomes, continues to grow. For example, the 1000 Genomes Project performed whole-genome sequencing of a geographically diverse set of 2,504 individuals, yielding a broad spectrum of genetic variation including over 88 million known variants. Incorporating all of these variants into a single graph reference yields regions of the graph that include a very large number of paths (reflecting significant variation in corresponding regions of the human genome) and, as a result, it is computationally expensive to align sequence reads to such regions. For example, in one dense region of a graph reference according to this data set, there are 48 nodes and approximately 262,000 (over a quarter million!) possible paths. Aligning sequence reads to a graph reference representing variation in this region may require evaluating each of the 262,000 paths, which can represent a significant impediment to alignment speed. Indeed, aligning even a single sequence read to this region can take up to an hour using conventional hardware, which is prohibitively expensive and makes aligning to a graph reference impractical even though the results of such an alignment may be useful.

Some embodiments described herein address all of the above-described issues that the inventors have recognized with conventional techniques for aligning sequence reads to a graph reference. However, not every embodiment described herein addresses every one of these issues, and some embodiments may not address any of them. As such, it should be appreciated that embodiments of the technology described herein are not limited to addressing all or any of the above-described issues of conventional techniques for aligning sequence reads to a reference or a graph reference.

The inventors have developed techniques for aligning sequence reads to a graph reference that significantly reduce the overall computational complexity of performing such an alignment, resulting in a significant increase in the speed of sequence read alignment. In some embodiments, rather than traversing every path through the graph reference, the traversal is modified such that paths which have previously been considered in the context of a current sequence read are removed from consideration. The modified traversal results in a smaller set of sequences to compare with the sequence read, greatly improving the efficiency of alignment. In further embodiments, the traversal is further modified such that only short segments, or k-mers, of a sequence read are aligned to the graph. Because these segments are shorter than the sequence read, fewer paths are evaluated by the graph traversal, thus reducing the search space and increasing the speed of traversal and resulting in a list of initial aligned locations which may be further extended to identify a best-fit location.

Further, the detailed description set forth below in connection with the appended drawings is intended as a description of embodiments and does not represent the only forms which may be constructed and/or utilized. However, it is to be understood that the same or equivalent functions and sequences may be accomplished by different embodiments that are also intended to be encompassed within the spirit and scope of the disclosure.

Graph Alignment System

FIG. 1 is a block diagram illustrating an embodiment of a graph alignment system 100 suitable for practicing exemplary embodiments of the present disclosure. The graph alignment system 100 may be used for aligning a plurality of sequence reads to a graph reference, such as a graph representing genomic variation across a plurality of individuals. In this embodiment, the graph alignment system 100 comprises a computing device 102, which may include a processor 104 in communication with a memory 106 over a bus 108. The memory 106 may store a plurality of sequence reads 112 generated from a genomic sample, and a graph reference 116. The graph reference 116 is a reference sequence construct that accounts for variations in genomic sequences within a species, population, or even among different cells in a single organism. The memory 106 may further include instructions or codes that when executed by the processor 104 implement an operating system 110 and a graph alignment engine 114.

Depending on particular implementation requirements of the present disclosure, the computing device 102 may be any type of computing system, such as a workstation, server, desktop computer, laptop, handheld computer, mobile device, cloud computing instance, or any other form of computing device or system. Further, the computing device 102 may have sufficient processing power and memory capacity to perform all or part of the operations described herein. Alternately, all of parts of the computing device 102 may be embodied as a stand-alone system, or as a component of a larger electronic system within any kind of environment. In certain embodiments, the graph alignment system 100 may comprise multiples of computing devices 102, which may be differently configured.

The processor 104 may include hardware or software-based logic to execute instructions on behalf of the computing device 102. For example, depending on specific implementation requirements, the processor 104 may include a microprocessor; single or multiple cores for executing software stored in the memory 106; an application-specific integrated circuit (ASIC); a graphics processing unit (GPU); a distributed processor, such as a cluster or network of processors or computing systems; a virtual or logical processor of a virtual machine; or other hardware or software components for controlling the computing device 102.

The memory 106 is a processor-readable medium that stores instructions, codes, data, or other information. As used herein, a processor-readable medium is any medium that stores instructions, codes, data, or other information non-transitorily and is directly or indirectly accessible to a processor. For example, the memory 106 can be a volatile random access memory (RAM), a persistent data store such as a hard-disk drive or a solid-state drive, a compact disc (CD), a digital versatile disc (DVD), a Secure Digital™ (SD) card, a virtual or networked drive, or any combination thereof. In some embodiments, the memory 106 can be integrated with the processor(s) 104, separate from the processor 104, or external to the graph alignment system 100.

Various applications, such as the graph alignment engine 114, may run on the operating system 110. The operating system 110 may comprise any of the versions of the conventional operating systems, any embedded operating system, any real-time operating system, any open source operating system, any proprietary operating system, or any other operating system capable of running on the computing device 102 and performing all or part of the operations described herein. Further, the operating system 110 and graph alignment engine 114 may in some instances be accessed or run from a bootable CD, thumb drive, or from a network.

Each sequence read 112 may comprise a sequence of contiguous nucleotide bases, which may symbolically be represented by the letters A, C, G, and T. The contiguous nucleotide bases represent a sequence that is "read" from a corresponding genomic sample, such as a DNA sample, RNA sample, ChIP-Seq sample, and the like. Typically, the sequence reads 112 will be obtained with the aid of a sequencer instrument, such as, for example, a Next Generation Sequencer (NGS) sequencer. Sequencing technologies and instruments are known in the art and include, for example, MiSeq® (Illumina, San Diego, Calif.), Ion Torrent® (Life Technologies, Carlsbad, Calif.), 454® (454 Life Sciences, Roche, Branford, Conn.), SOLiD® (Applied Biosystems, Thermo Fisher Scientific, Foster City, Calif.), tSMS™ (Helicos BioSciences, Cambridge, Mass.), SMRT® (Pacific Biosciences, Menlo Park, Calif.), and chemFET techniques. Sequence reads 112 may be stored in the memory 106, or alternately may be accessed from another location (e.g., over a network). Sequence reads 112 are often stored in an electronic format, such as in a FASTA or FASTQ file.

In general, a nucleotide sequence read 112 that is being analyzed according to the disclosure will have a length of about 50 to about 500 nucleotides. For example, a nucleotide sequence read can have a length of about 50, about 100, about 150, about 200, about 250, about 300, about 350, about 400, about 450, or about 500 nucleotides. In some embodiments, sequence reads 112 include at least 50 base pairs (e.g., 50 base pairs, 100 base pairs, 200 base pairs, 500 base pairs). In further embodiments, sequence reads 112 may be longer (e.g., 100 base pairs or more, 500 base pairs or more, 1,000 base pairs or more, 5,000 base pairs or more, and 10,000 base pairs or more). For example, certain "long read" next-generation sequencing technologies, such as PacBio® Single Molecule, Real-Time (SMRT) Sequencing, can generate sequence reads that range from 10,000 to 60,000 base pairs. In certain examples, the sequence reads 112 may comprise a variety of combinations of lengths.

The graph alignment engine 114 may comprise a library of logical and statistical code that, when loaded into memory 106 and executed by processor 104, aligns the plurality of sequence reads 112 against the graph reference 116. The term "alignment" can refer to identifying an optimal, or best-fit, position of a sequence read 112 when the sequence read is positioned against a reference sequence. For example, an optimal position can be one in which when the sequence read is placed at that position such that the nucleotide sequences overlap, the sequence read exhibits substantial similarity with the graph reference. This may also include the addition of gaps. Sequence read alignment is known in the art, and various techniques exist. Well known sequence read alignment algorithms include the Smith-Waterman and Needleman-Wunsch algorithms, which identify an optimal alignment by computing scores for possible alignments and then finding the best-fit alignment via dynamic programming. Certain algorithms apply a hash function to either the reference sequence or the sequence read, and then search for positions at which the hash values match. Other algorithms may employ suffix or prefix tries. See Heng Li and Nils Homer, A Survey of Sequence Alignment Algorithms for Next-Generation Sequencing, Brief. Bioinform. 2010 September; 11(5):473-483. As will be described in further detail below, certain pattern or string matching algorithms (such as the Boyer-Moore and Tarhio-Ukkonen algorithms) may also be used to identify the most likely position of a pattern (the sequence read) against a text (the reference sequence).

The inventors have appreciated that alignment to a graph reference, as opposed to a conventional linear reference sequence, is a complex process requiring many additional considerations. In many conventional genomics applications, sequence reads 112 are aligned to a linear reference sequence, such as the GRCh38 human genome assembly. However, the use of linear reference sequences in alignment can result in reference bias, in which the alignment algorithm may force placement and therefore misalign reads. Further, sequence reads from a sample with low homology to the reference may result in a high percentage of reads being unaligned. These factors lead to low discovery and concordance rates for many variants, such as short insertions and deletions ("indels") and structural variants. As previously noted, reference alignment with graph references solves many of these problems by accounting for variations as alternate paths or branches through the graph. In contrast to a conventional linear reference sequence, a graph reference 116 is a reference sequence construct that can represent a reference sequence and possible variations from that reference sequence. The graph reference 116 accounts for variability within the reference sequencing by allowing for two or more alternative sequences at various positions within the reference sequence.

Figure 2:
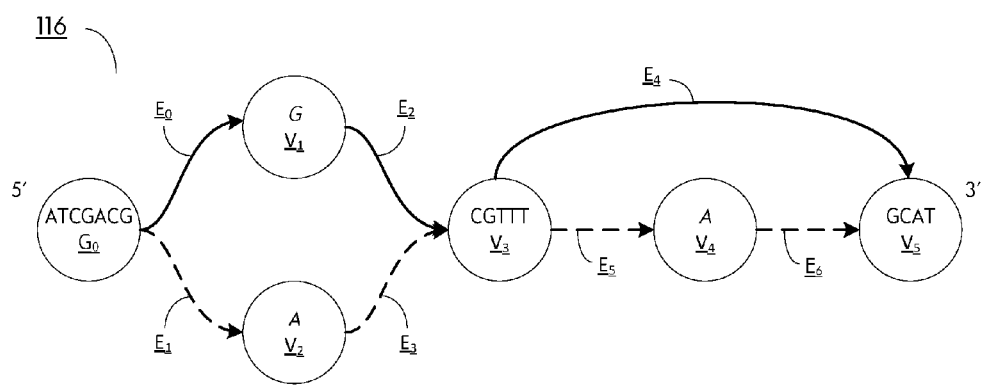

FIG. 2 illustrates an exemplary embodiment of a graph reference 116. In this embodiment, the graph reference 116 represents a hypothetical region of the human genome. However, graph references according to the disclosure can represent any sequence of symbols, including nucleotide sequences and protein sequences from various organisms, as the disclosure is not limited in this respect.

As shown in FIG. 2, the graph reference 116 comprises a plurality of nodes, or vertices, $\{V_0, \ldots, V_5\}$ connected by a plurality of directed edges $\{E_0, \ldots, E_5\}$. A node of the graph can encode a substring, such as a nucleotide or protein sequence. The directed edges specify an order in which the substrings of each node may be concatenated together, corresponding to the 5'-3' directionality of RNA and DNA strands. Stated differently, edges of the graph can encode instructions for concatenating nucleotide sequences associated with each node together. As the edges are directed, valid nucleotide sequences may be generated by traversing the graph in a specific direction, according to the 5'-3' directionality.

As shown in this embodiment, the graph reference 116 is a directed acyclic graph (DAG), such that there are no paths through the graph which follow through the same node twice. (In other words, there are no cycles.) This property is useful for representing genomic sequences by constraining the set of possible paths, and thus constraining the set of possible nucleotide sequences that can be generated from the graph. However, in certain embodiments, allowing cycles may help in simplifying the representation of repeats, for example. As the graph reference 116 encodes a sequence and variation, in certain embodiments it may also be referred to as a sequence variation graph, or SVG.

In certain embodiments, the graph reference 116 may be a subgraph, or "local" graph, of a larger graph reference. For example, the graph reference 116 may be a local region of a human genome graph reference that is first identified by a separate algorithm, such as a "global" search algorithm that identifies an initial list of plausible locations of the sequence read for alignment.

In certain embodiments, the graph reference 116 may be generated by providing a linear reference sequence and a set of variations from the reference sequence. The variations can comprise single nucleotide polymorphisms (SNPs), insertions and deletions (indels), and structural variants (SVs). A directed acyclic graph is generated by transforming the linear reference sequence into an initial graph, and subsequently adding nodes and edges representing the variations to the initial graph to obtain a directed acyclic graph reflecting the linear reference sequence and the set of variants. The graph may further be updated by adding a set of one or more alternative sequences reflecting the set of variants. Typically, the original linear reference sequence may be designated as a "base," or "backbone," path or branch. Any alternate path representing variation will then converge to the backbone branch. Methods for creating such a reference sequence construct may be found, for example, in U.S. Patent Publication No. 2015-0057946, incorporated by reference in its entirety.

The graph reference 116 can further have the property that there must be at least one source node and at least one sink node, such that every edge and every node in the graph belongs to at least one directed path between a source and a sink. As shown in the graph reference 116 of FIG. 2, the source (or "first" node) is $V_0$, and the sink (or "last") node is $V_5$. While a graph reference 116 may have multiple sources and sinks, typically a graph reference representing nucleotide sequence and genomic variation will include a single source and sink such that all possible paths begin at the source node and end at the sink node. In such cases, the graph has no orphan or leaf nodes, such that all possible paths from a given node will eventually converge back to the backbone branch (e.g., in the case of a graph reference representing the human genome, the backbone branch could represent the GRCh38 human genome assembly reference sequence). However, as will be described in further detail below, the aligned position of a sequence read may also be described according to a path through a graph, e.g., spanning one or more nodes. In this case, the aligned position or path of the sequence read will only span a few nodes in the graph (e.g., one or more).

As noted above, often a graph reference will include a base path that represents a linear reference sequence. For example, as shown in FIG. 2, the graph reference 116 has a path including nodes $\{V_0, V_1, V_3, V_5\}$, which according to the instructions encoded by edges $\{E_0, E_2, E_4\}$ (shown as solid lines) results in the concatenated nucleotide sequence "ATCGACGGCGTTTGCAT". This concatenated nucleotide sequence may represent a known linear nucleotide sequence. Similarly, a graph reference representing the human genome may include a base path that represents the GRCh38 human genome assembly. Variations from this sequence ("variants"), such as single nucleotide polymorphisms (SNPs), short insertions and deletions ("indels") and larger structural variants are represented as alternate nodes. Paths through the graph including these nodes represent variations of the linear nucleotide sequence; concatenating the nucleotide sequences associated with these nodes according to the edges results in a nucleotide sequence including that variant. For example, as shown in FIG. 2, a path including nodes $\{V_0, V_2, V_3, V_4, V_5\}$ that traverses edges $\{E_1, E_3, E_5, E_6\}$ (shown as dotted lines) encodes a sequence that represents a "G to A" single nucleotide polymorphism (SNP) (represented by node $V_2$), and a single base pair insertion of an A nucleotide (represented by node $V_4$), resulting in the concatenated sequence "ATCGACGACGTTTAGCAT". Substrings of these concatenated sequences may be compared to a given sequence read to identify positions for alignment.

The graph reference 116 represents variations of a relatively short reference sequence (here, 17 base pairs, or "bp"). However, in certain embodiments, a graph reference may represent a genome of an organism, or only a portion of a genome, e.g., a chromosome, or a smaller segment of genomic information. In some embodiments, the graph may represent greater than 1,000 nucleic acids, e.g. greater than 10,000 nucleic acids, e.g. greater than 100,000 nucleic acids, e.g. greater than 1,000,000 nucleic acids. A graph reference 116 may represent a species (e.g., homo sapiens) or a selected population (e.g., people having breast cancer), or even smaller populations, such as genomic variation among different tumor cells (e.g., germline, tumor, relapse) in the same individual.

In practice, the graph reference 116 may be represented and stored in a computer memory, such as the computer memory 106 of FIG. 1. For example, a node can be a portion of the memory 106, which can include entries within a database, files or portions of one or more files within a file system, and the like. More specifically, a node can be one or more memory locations at which properties or characteristics of that node (e.g., a sequence of nucleotide symbols) and references or relationships between that node and other nodes (e.g., information describing a set of parent or child nodes) are stored. These relationships and references between nodes can be referred to as the edges of the graph. As a specific example, a node can be a portion of a memory at which a list of edges of that node (or edges adjacent to or incident upon that node) are stored.

For example, in one embodiment, a graph reference can be represented as an N×N matrix of binary values, where N is the number of nodes in the graph. The value located at the intersection of each column and row represents whether an edge exists between that node (represented by the column) and another node (represented by the row). As another example, each node may be stored in the memory 106 as a data object that includes a node identifier, an associated nucleotide sequence, and a set of related nodes (such as a set of parent or child nodes). This information can be represented as a tuple, e.g.: $(V_3, CGTTT, (V_4, V_5))$, which describes node $V_3$ of the graph reference 116 of FIG. 2. The set of related nodes can comprise pointers to physical locations in memory storing those related nodes, such that dereferencing a pointer results in the actions of following an edge and traversing the graph. In other embodiments, graphs may also be stored using adjacency lists, index-free adjacency techniques, and the like.

The graph reference 116 may also be serialized into a format that may be read by a processor to instantiate a graph into a memory (such as the processor 104 and memory 106 of the graph alignment system 100 of FIG. 1). A description of a graph may be represented in a variety of formats. For example, a graph reference can be described in a JavaScript Object Notation (JSON) document, a YAML Ain't Markup Language (YAML) document, or an eXtensible Markup Language (XML) document. Each of these formats allows for the storage of various elements or attributes of nodes, such as node identifiers, sets of related nodes, a nucleotide sequence, and other information. Serializing graphs according to these formats aids in handling of the graph by the graph alignment system 100. For example, in certain embodiments, the graph alignment engine 114 may access a description of the graph reference 116 (e.g., in a JSON file transferred over a network), instantiate the graph reference 116 as one or more objects in the memory 106, and then align the set of sequence reads 112 against the graph reference 116. Various other formats may also be used, including compressed formats, for example.

The graph reference 116 associates nucleotide sequences with the nodes, and thus may be referred to as a node-based graph. However, in certain embodiments, nucleotide sequences may instead by associated with the edges, which would describe an edge-based graph. In other embodiments, nucleotide sequences may be associated with both edges and nodes. Further, certain nodes and/or edges may lack a nucleotide sequence (e.g., an alternate node that encodes a deletion or gap in the underlying reference sequence). Nodes and edges in the graph may also be associated with other metadata elements, such as the observed allele frequency in a population, association with certain diseases (e.g., cancer), pedigree information, and the like. In certain embodiments, nodes and edges may store additional information, including whether a node has been previously visited by a graph traversal, or whether child nodes have been previously followed according to a current traversal. Similarly, additional information may be distributed across nodes and edges. For example, a node may store information indicating whether it has been visited by a previous graph traversal, and an edge may store information indicating whether it has been recently followed. The disclosure is not intended to be limiting in this respect.

Figure 3:
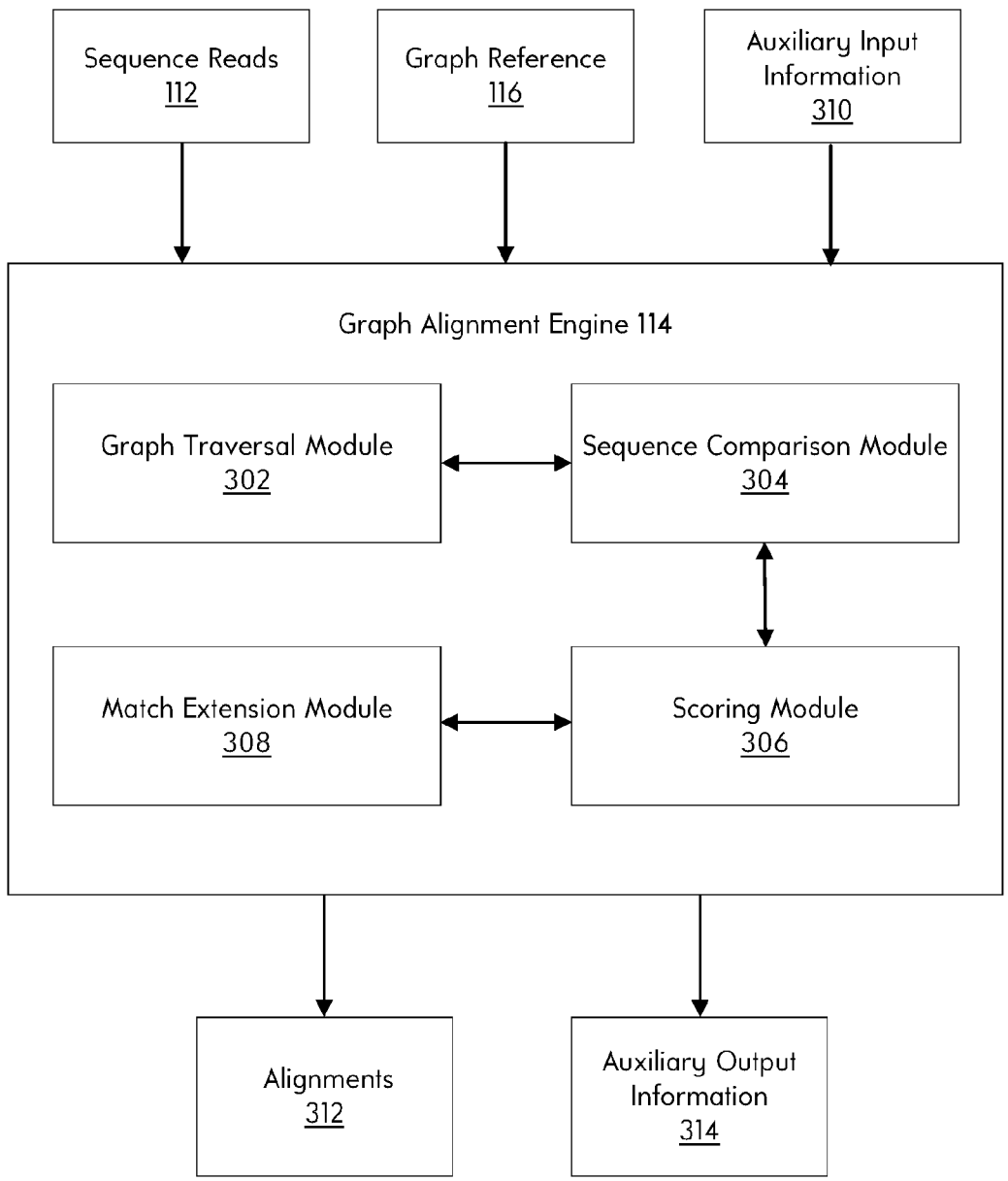

FIG. 3 illustrates the graph alignment engine 114 in further detail. As shown in FIG. 3, the graph alignment engine 114 can further comprise a graph traversal module 302, a sequence comparison module 304, a scoring module 306, and a match extension module 308. Each of the modules can comprise a library of logical and statistical code that, when loaded into a memory and executed by a processor, perform various functions associated with aligning a plurality of sequence reads against a graph reference. The primary inputs to the graph alignment engine 114 include a set of sequence reads 112, a graph reference 116, and auxiliary input information 310. As the sequence reads 112 are aligned to the graph reference 116, sequence read alignments 312 and auxiliary output information 314 are generated. The auxiliary input information 310 can be, for example, one or more parameters or files provided to the graph alignment engine 114.

Each of the modules 302, 304, 306, 308 describe programs or software that implement various functions that may be associated with a graph alignment system according to the disclosure. The terms "program" or "software" are used herein in a generic sense to refer to any type of computer code or set of processor-executable instructions that can be employed to program a computer or other processor to implement various aspects of embodiments as discussed herein. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein. Accordingly, while the present disclosure is illustrated with reference to the modules 302, 304, 306, 308, as will be appreciated by those of skill in the art, other configurations and/or combinations fall within the scope of the disclosure.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

Graph Traversal

The graph traversal module 302 is configured to traverse a graph reference, such as the graph reference 116 of FIG. 2, to identify a plurality of paths. Traversing (which may also be referred to as "searching" or "walking" along a graph reference) may refer to identifying a plurality of paths within the graph reference, which may be performed by accessing the nodes in the graph reference 116 in a particular order or sequence by following the outgoing edges of successive nodes. As nodes are accessed, nucleotide sequences may be generated by concatenating the sequences associated with each node together according to the followed edges. These generated sequences, or substrings thereof, may then be compared to a sequence read 112 by the sequence comparison module 304, for example.

The graph traversal can include a variety of searching methods, such as a depth-first search. Briefly, a depth-first search is an algorithm for traversing a graph that begins at a root node, such as the source node. The algorithm then proceeds to follow directed edges as far as possible until a node with no outgoing edges is reached. The algorithm then "backtracks" by moving backwards against the previously followed edge to the previously accessed node, and considering whether there are any unfollowed edges from that previously accessed node. The depth-first search enumerates each possible path in the graph, and terminates once all unique paths have been identified. Stated differently, the depth-first search can terminate once it attempts to backtrack from the root node, or the node from which the depth-first search began.

The root node will typically be the source node, though methods according to the disclosure could also begin at another arbitrarily selected node (e.g., by beginning the search at a particular position in the graph). In certain embodiments, the source node added to the search path may be the first node in a graph. In other embodiments, the source node may be another node in the graph. For example, the algorithm could select a 5' source node and a 3' sink node corresponding to a subset or subgraph of the graph reference (e.g., a "local" region or graph of a larger graph reference). When aligning sequence reads to a graph reference, indications of these nodes could be provided along with the larger graph reference. Alternately, a subgraph may be generated from the larger graph reference and then provided.

While the present disclosure refers to a depth-first search, other graph traversal techniques could also be used to walk across a graph reference and identify paths. In certain embodiments, a graph traversal module according to the disclosure could utilize a breadth-first search, for example.

In certain examples, traversing a graph may further comprise updating and/or identifying values stored or associated with each node. For example, the graph traversal module 302 may consider a followed indicator associated with each node (e.g., stored with, or as an entry in a table or database) that indicates which of the child nodes from that node have already been visited by a current depth-first search. In one embodiment, the followed indicator can be a counter that starts at zero and increments as edges are traversed. For example, for a node having two child nodes, a counter for that node is incremented by one on a first traversal of an outgoing edge. When the algorithm later backtracks to that node, it considers the counter and notes that the first directed edge has already been traversed. The algorithm then follows the second outgoing edge and increments the counter again. When the algorithm later returns to that node after backtracking from the second outgoing edge, it notes that both child nodes have already been considered (because, for example, the value of the counter is "2"). Because both child nodes have already been considered, the algorithm then backtracks from that node. Further, when backtracking, the algorithm may reset the counter for that node to zero. This allows for future considerations of that node, which may include different combinations of upstream nodes, to consider all downstream paths.

It should be noted that a followed indicator according to the disclosure may be implemented in a variety of ways. A followed indicator can be any indication of which outgoing edges (and thus, child nodes) have not yet been considered by a current search path. For example, in certain embodiments, a followed indicator may be associated with each outgoing edge. This could simply be a 1-bit flag, e.g., "1" represents that the edge has been followed, and "0" represents that it has not. In further embodiments, a followed indicator may comprise a table or index specifying which outgoing edges have been considered as part of the current search.

Figure 4:
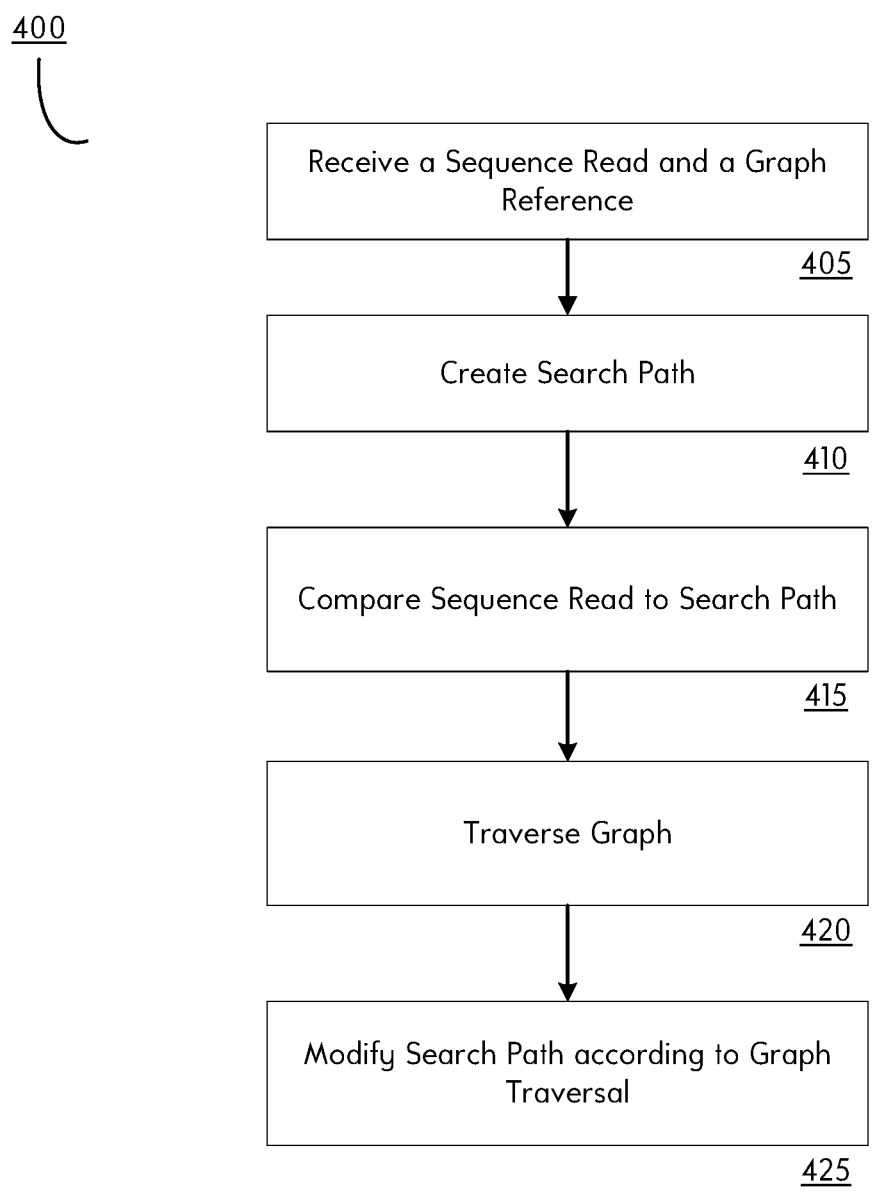

In some embodiments, the graph traversal module 302 may maintain and update a search path, or set of nodes, during a graph traversal. The search path corresponds to a current set of nodes that are being considered by a depth-first search, which are selected by following a path through the graph reference 116. FIG. 4 depicts an illustrative method 400 of aligning a sequence read to a graph reference according to an embodiment of the disclosure. The method 400 can be practiced by a graph alignment engine executing on a processor, such as the graph alignment engine 114 and processor 104 of FIG. 1. However, like other methods according to the disclosure, the method 400 may be performed by any suitable computing device(s) (e.g., a single computing device, multiple computing devices co-located in a single physical locations or located in multiple physical locations remote from one another, one or more computing devices part of a cloud computing system, etc.), as aspects of the technology described herein are not limited in this respect.

The method 400 can begin at act 405 by receiving a sequence read and a graph reference. The sequence reads may be obtained by sequencing one or more biological or genomic samples obtained from an individual or organism, for example, by using next generation sequencing and/or any other suitable sequencing technique or technology, as aspects of the technology described herein are not limited by the manner in which the sequence reads are obtained.

A search path is then created at act 410. The search path can comprise one or more nodes of the graph reference 116, and may be stored as a component of a vector, array, ordered list, or other form of data structure. Initially, the search path can comprise the source node of the graph reference 116. The sequence read 112 is then compared to the search path at act 415, e.g., by comparing substrings of the concatenation of the nucleotide sequences associated with each node in the search path with the sequence read 112. Once all comparisons have been made, the graph is then traversed at act 420, e.g. by identifying child nodes of the source node that have not yet been considered as part of the current search path, or backtracking. The search path is then modified at act 425 according to the graph traversal, e.g., by adding a child node to the search path, removing the most recently added node, or removing one or more nodes.

Figure 5:
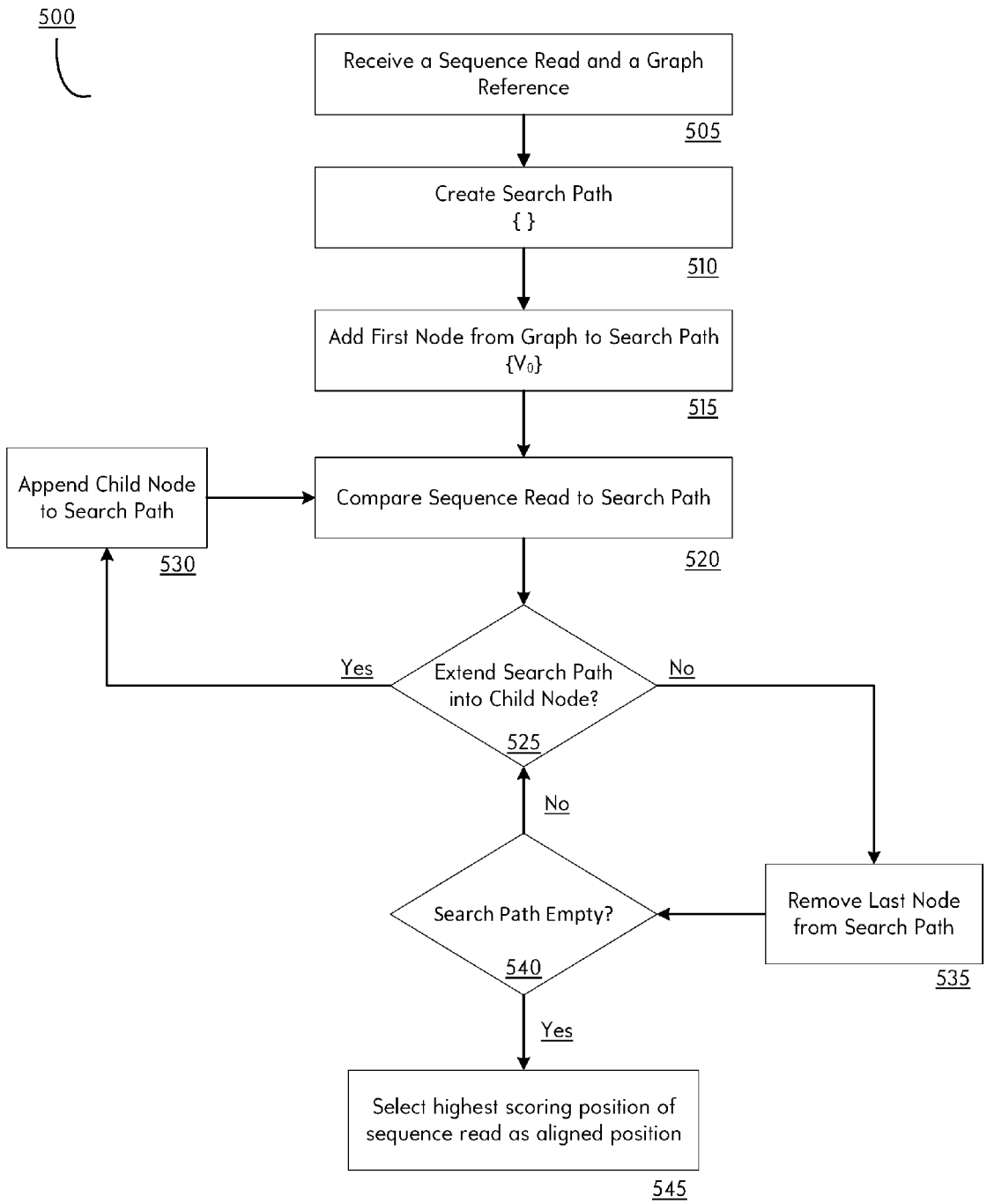

FIG. 5 depicts another embodiment of a method 500 of aligning a sequence read to a graph reference. Like the method 400 of FIG. 4, the method 500 may be performed in the context of a graph alignment system 100, and practiced at least in part by a graph alignment engine 114, or any other suitable computing device(s), for example. The method 500 can begin at act 505 by receiving (e.g., by a graph alignment engine 114) a sequence read and a graph reference (e.g., a sequence read of the plurality of sequence reads 112 and the graph reference 116). Next, method 500 proceeds to act 510, where a search path is created. As shown, the search path may initially be an empty set ("{ }"). A first node from the graph is then added to the search path at act 515. The sequence read is then compared to the search path at act 520, i.e., by considering potential matches between the nucleotide sequence represented by the search path and the sequence read.

Once all or any possible comparisons have been made, the method 500 considers at decision 525 whether the search path can be extended by adding a child node of the last node in the current search path. If this is possible (e.g., because the last node has at least one previously unfollowed node), the child node is appended to the search path at act 530, such that the search path may again be compared to the sequence read at act 520. However, if the search path cannot be extended into any child nodes (e.g., because all child nodes have already been followed as part of this search path, or the last node has no child nodes), the last node is removed from the search path at act 535. In other words, the method 500 backtracks at act 535, as in a depth-first search.

The method 500 then proceeds by considering whether the search path is empty at decision 540, which can occur when the first node added to the search path has been removed. If the search path is not empty, the method 500 attempts to extend the search path into a previously unfollowed child node at decision 525. However, if the search path is empty, then there are no additional child nodes to consider. At this stage, all possible paths through the graph have been considered, and thus traversal of the graph may end. The method 500 may then select the highest scoring position of the sequence read as the aligned, or mapped position at act 455.

Figure 6A:
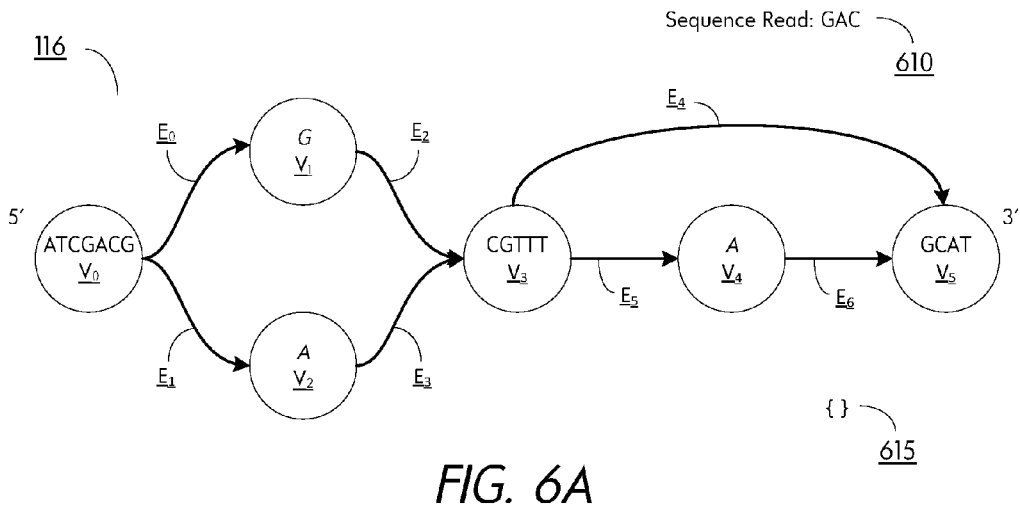
FIGS. 6A-E are illustrative diagrams of a graph-based reference sequence construct during a graph traversal in accordance with some embodiments of the technology described herein.

An application of the method 500, as practiced by a graph alignment engine (such as the graph alignment engine 114 of FIG. 3) will now be described with respect to FIGS. 6A-E, which depict an exemplary graph reference 116 and a sequence read 610 (here, the nucleotide sequence "GAC") to be aligned. As briefly described above with respect to FIG. 2, the graph reference 116 is a directed acyclic graph that describes a fictional portion of a genome or other nucleotide sequence. As shown in FIG. 6A, the graph reference 116 comprises a set of vertices and edges, {V, E}, including six vertices $\{V_0, \ldots, V_5\}$ connected by six edges $\{E_0, \ldots, E_5\}$. $V_0$ is the first, or "source" node, and represents a short upstream (5') nucleotide sequence ATCGACG. Nodes $V_1$ and $V_2$ represent a pair of alternate sequences (i.e., the reference sequence and a variation) from a single nucleotide polymorphism ("SNP"). Here, the reference sequence is the nucleotide "G", and the variation is the nucleotide "A". In vertex $V_3$, the graph converges to a conserved sequence CGTTT, followed by an insertion event of a single A in node $V_4$, and finally a short downstream (3') sequence GCAT in the end, or "sink", node $V_5$. The process of alignment, or mapping, is to identify potential matches between the sequence read 610 and locations within the graph reference 116.

A typical depth-first search of a graph or tree structure is concerned with traversing each possible path through a graph by visiting each node. However, a depth-first search as performed by the graph traversal module 302 of FIG. 3 and method 500 of FIG. 5 differs in that it searches while also considering a sequence read, which represents a sequence, or string, of symbols. Thus, possible aligned positions of the sequence read may span multiple nodes in a search path, requiring combinations of those nodes to be evaluated simultaneously. For example, the sequence read 610 may align to a sequence generated by concatenating nucleotide sequences from vertices $V_0$, $V_1$, and $V_3$ together, or alternately may align to one generated by concatenating sequences from vertices $V_0$, $V_2$, and $V_3$. In this embodiment, this is performed by maintaining a set of vertices in a search path 615. The nucleotide sequences associated with the nodes in the search path 615 may be concatenated together to form a sequence that may be considered for matches to the sequence read 610.

Figure 6B:
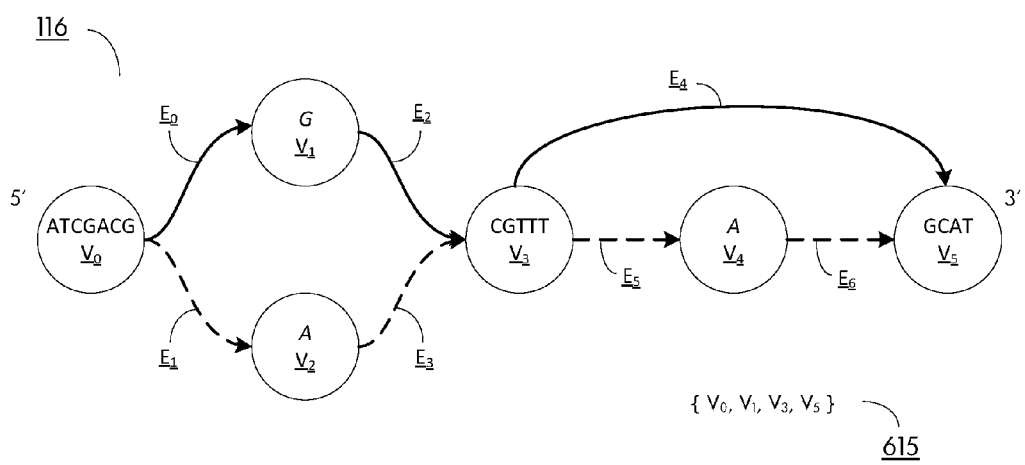

To begin, node $V_0$ is added to the search path as a first, or source node (e.g., act 515 of the method 500 of FIG. 5). There are five possible 3-bp substrings within $V_0$: ATC, TCG, CGA, GAC, and ACG. (Note that not all possible substrings may require evaluation, as will be described in more detail below with respect to the sequence comparison module 304 of FIG. 3.) Once we consider each substring against the sequence read 610 ("GAC"), there is no additional sequence to consider in the given search path. Accordingly, the graph traversal module 302 attempts to extend the search path into a child node of the last node of the current search path, i.e., $V_0$ (e.g., decision 525). The graph traversal module 302 then considers the child nodes of $V_0$, which are $V_1$ and $V_2$. $V_1$ is selected and added to the search path 615 (e.g., act 530). Accordingly, the search path is now $\{V_0, V_1\}$, representing the nucleotide sequence (by virtue of concatenating the sequences associated with each node) ATCGACGG (the sequence for node $V_1$ is underlined to indicate its position in the concatenated sequence). This yields an additional 3-bp substring (CGG) for comparison (e.g., act 520). Once considered, the graph traversal module continues by adding node $V_3$ to the search path, yielding additional substrings GGC, GCG, CGT, GTT, and TTT. Note that, from the perspective of the alignment algorithm, the substring GGC comprises sequence from three separate nodes, GCG two, and the remainder one. Once these substrings are evaluated, node $V_5$ is then added to the search path. FIG. 6B illustrates the search path 615 at this stage, comprising nodes $V_0$, $V_1$, $V_3$, and $V_5$.

Figure 6C:
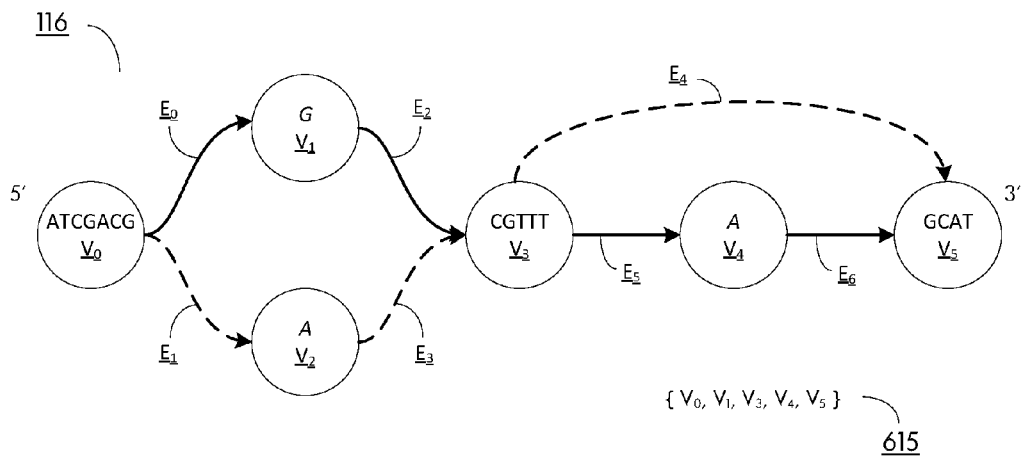

Once any sequence including node $V_5$ is considered, the algorithm again attempts to extend the search path. However, node $V_5$ has no children, and thus the algorithm cannot extend the search into a child node (e.g., decision 525 of the method 500 of FIG. 5). At this stage, the algorithm "backtracks" to find new paths by removing the last node $V_5$ from the end of the search path (e.g., act 535), and then attempts to extend again from node $V_3$. As the second path from node $V_3$ has not yet been considered, the graph traversal module 302 proceeds to add nodes $V_4$ and then $V_5$ to the search path, yielding new sequences for comparison to the sequence read 610 that include the "A" nucleotide from node $V_4$. As shown in FIG. 6C, the search path now includes nodes $V_0$, $V_1$, $V_3$, $V_4$, and $V_5$.

Figure 6D:
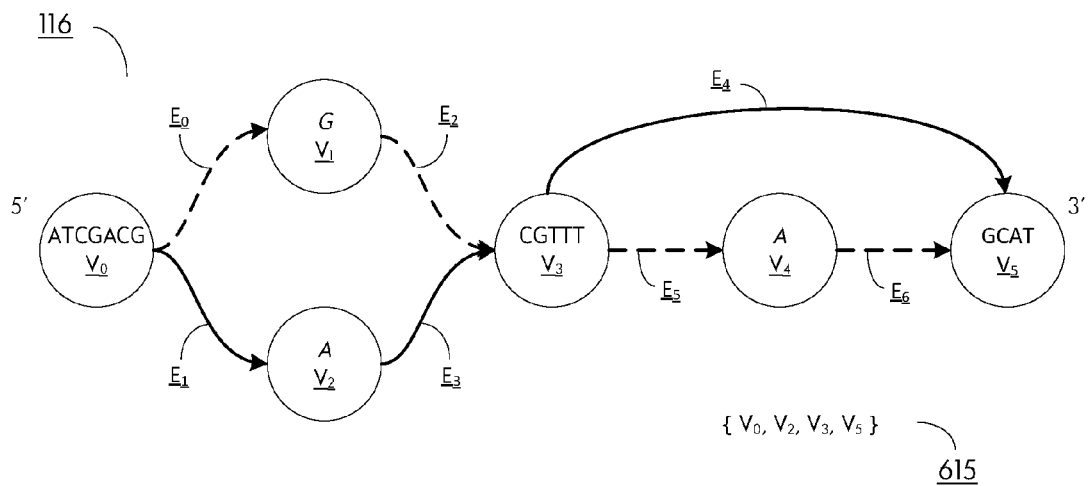
Figure 6E:
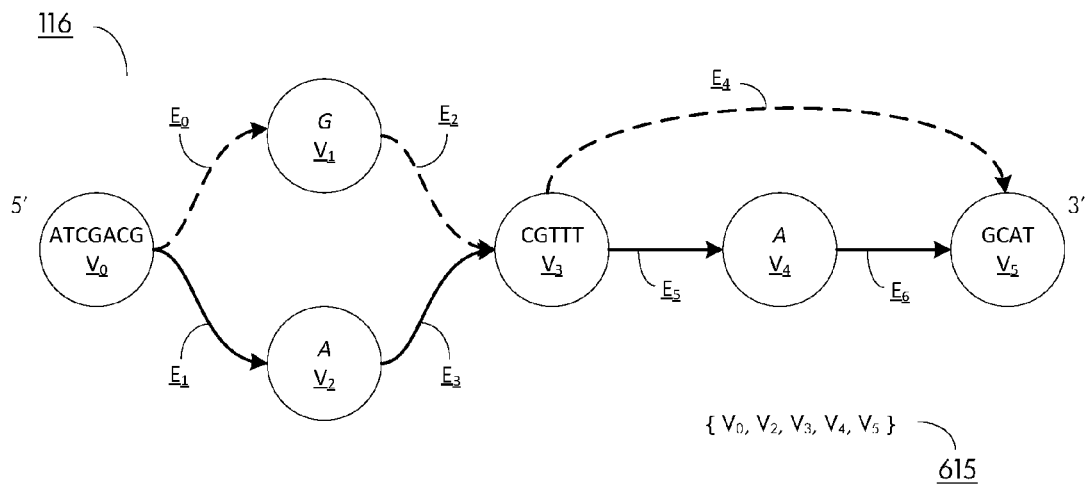

At this stage of traversal, each of the above search paths has yet to consider a set of nodes in combination with node $V_2$, representing a SNP in the reference sequence. The graph traversal module 302 continues to backtrack (e.g., according to decision 525 and act 535 of the method 500) until the search path includes only node $V_0$. Node $V_2$ is then added as a previously unfollowed child node of $V_0$ (e.g., act 530). The search path is then modified as previously described, identifying new combinations of nodes representing new nucleotide sequences for comparison with the sequence read 610, resulting in the search paths as shown in FIGS. 6D-E. Upon reaching the search path 615 shown in FIG. 6E, all paths through the graph have been considered. Accordingly, the graph traversal module 302 will backtrack beyond node $V_0$, resulting in an empty search path. At this stage, the graph traversal is complete.

While in this example, substrings are generated from concatenated nucleotide sequences, in certain embodiments, substrings may be generated directly, i.e. by concatenating nucleotide sequences from nodes up to the length of a desired substring (which may be, for example, approximately the length of a sequence read). The disclosure is not meant to be limiting in this respect.

In certain embodiments, the graph traversal may be modified such that paths containing nucleotide sequences which have already been considered are preemptively removed from consideration. This may include marking a node as "visited" (e.g., by setting an indicator, variable, or flag associated with the representation of that node in the memory) when the algorithm backtracks from that node. Subsequent sequence comparisons that include sequence generated only from visited nodes (i.e., nodes marked as "visited") have already been considered and may be omitted. In such cases, the algorithm may preemptively backtrack from a first visited node, rather than attempt to extend the search through all downstream paths from that node, even when the particular current search path has not yet been considered.

Figure 7A:
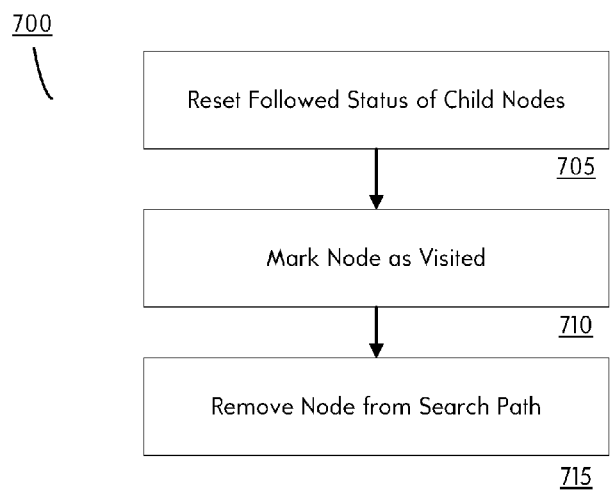
FIG. 7A is a flow diagram illustrating a method of removing a node from a search path.

FIG. 7A depicts an embodiment of a method 700 of removing a node from a search path. The method 700 represents an improvement to searching and traversal of graph references, in which nodes for which all downstream paths have already been considered are marked as visited when backtracking. Once it is determined that a search path cannot be extended into a child node (e.g., because the last node does not have any child nodes, or all of the child nodes of the last node have already been followed), the "followed" status of those nodes is reset at act 705. As previously described, the "followed" status may be an indicator or counter associated with each node that indicates which of the child nodes have already been followed. In systems and methods according to the disclosure, the followed status may be reset when backtracking such that future paths may evaluate downstream nodes in evaluation with new combinations of upstream nodes.

Additionally, as shown in FIG. 7A, the last node is then marked as "visited" at act 710, and subsequently removed from the search path at act 715. Marking a node as visited indicates that all of the downstream paths, starting from that node, have previously been considered by the depth-first search. In other words, any nucleotide sequences starting with a node or set of nodes that are "visited" have previously been evaluated. (Note that a visited node may still be evaluated in combination with unvisited nodes, which would generate an unevaluated nucleotide sequence.) Like the "followed" indicators as previously described, marking a node as "visited" can be modifying a "visited" indicator or flag stored with each node. Such an indicator may be also stored separately, e.g., in a database, flat file, table, index, and the like.

Figure 7B:
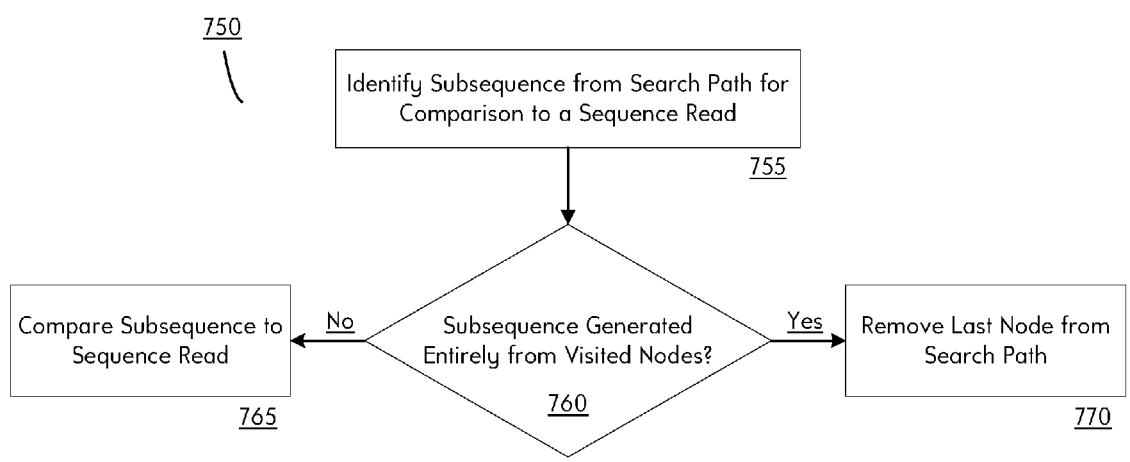
FIG. 7B is a flow diagram illustrating a method of comparing a sequence read to a search path, in accordance with some embodiments of the technology described herein.

This information can later be used to remove certain paths from comparison, limiting the depth-first search and reducing the number of comparisons performed to identify aligned positions of sequence reads within a graph reference. For example, FIG. 7B depicts an embodiment of a method 750 of comparing a sequence read to a search path. The method 750 can begin at act 755 by identifying a subsequence, or substring, from a search path for comparison to a sequence read. As previously noted, this can involve identifying unique substrings within the search path, wherein the unique substrings may be generated from a concatenated sequence of the nucleotide sequences associated with the nodes currently in the search path. The method 750 then considers at act 760 whether the subsequence currently being considered has been generated entirely from visited nodes. If it has not (i.e., at least one nucleotide of the current subsequence is generated from a node that is not marked as visited), the subsequence is compared to the sequence read to determine whether it constitutes a match at act 765. However, if the subsequence has been generated entirely from visited nodes, then the last node of the search path (i.e., the most recently added node to the search path) is removed from the current search path at act 770. In other words, the graph traversal is modified such that the search prematurely backtracks when the current subsequence being considered is generated only from nodes marked as visited (i.e., "visited nodes"). The search may then proceed by attempting to extend the search path into a child node of the last node of the modified search path (e.g., according to decision 525 of the method 500 of FIG. 5).

The inventors have appreciated that marking certain nodes as "visited", and then modifying the search path when a current subsequence is generated entirely from nodes marked as visited, is a significant feature that greatly improves both the efficiency and speed of a depth-first search. The visited status indicates that each of the nodes downstream from and including that node have previously been considered by the traversal. When generating a subsequence for comparison to a sequence read, if all of the nodes generating that subsequence are marked as visited, it is definitive that the generated subsequence has previously been considered by the depth-first search, and thus the search path is modified to preemptively remove downstream nodes (and corresponding subsequences) from further consideration. The method 750 thus proceeds to "backtrack" early, rather than progress to consider further paths downstream from that node.

As shown in this embodiment, downstream nodes marked as visited may still be considered as part of a traversal. This occurs when a given subsequence is generated from at least one node that has not been visited. For example, if a sequence read extends through several nodes, as long as one node has not been visited, the traversal and comparison continues because the generated subsequence is unique and should be evaluated. In this embodiment, this is why the "followed" indicators are reset (e.g., at act 705), thus allowing for future considerations of visited nodes with potentially unvisited upstream nodes.

Figure 8A:
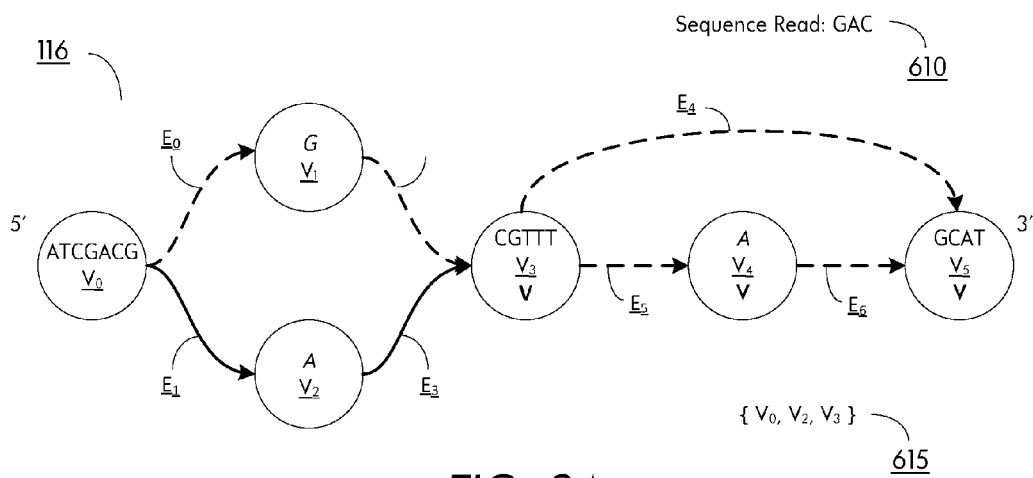
FIGS. 8A-B are illustrative diagrams of a graph-based reference sequence construct during a modified graph traversal in accordance with some embodiments of the technology described herein.
Figure 8B:
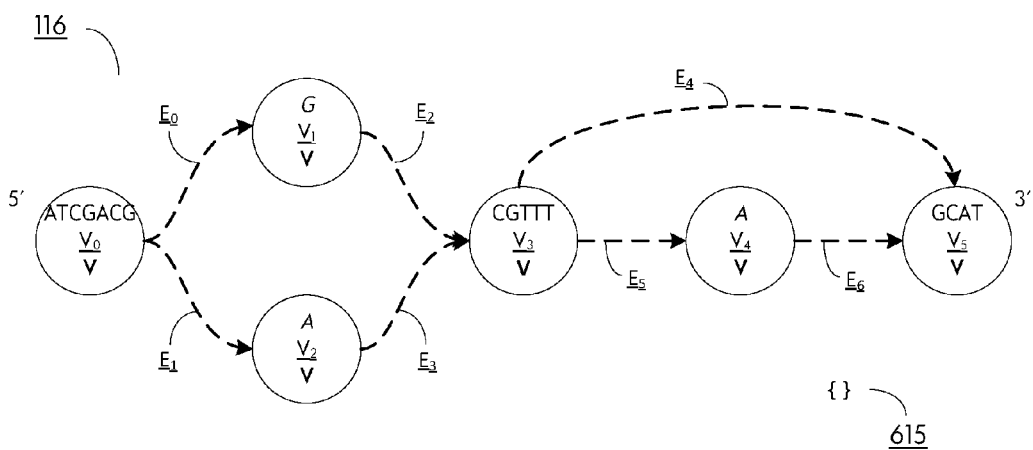

FIGS. 8A-C depict the graph reference 116 of FIG. 2 and illustrate an application of the methods 700, 750 of FIG. 7. Consider a state of a graph traversal that has previously considered the search path $\{V_0, V_1, V_3, V_5\}$ (e.g., FIG. 6B), and is now considering the search path $\{V_0, V_1, V_3, V_4, V_5\}$ (e.g., FIG. 6C). The graph traversal module 302 backtracks from node $V_5$ to $V_4$, and then backtracks from node $V_4$ to $V_3$. Node $V_3$ has no previously unfollowed child nodes, so the followed status of those nodes is reset (e.g., act 705). Node $V_3$ is then marked as visited (e.g., act 710), and the graph traversal module 302 proceeds to backtrack to node $V_0$. (Similarly, nodes $V_4$ and $V_5$ in this example were marked as visited during backtracking as they satisfy the same criteria.) The graph traversal module 302 then begins to follow previously unfollowed paths. From node $V_0$, nodes $V_2$ and $V_3$ are added. FIG. 8A depicts the state of the graph reference 116 and search path 615 at this stage of traversal.

Once node $V_3$ has been added to the search path 615, sequences generated by concatenating the nucleotide sequences associated with the nodes of the search path now include subsequences generated from a node that is marked as visited ("V"). Possible 3-bp subsequences that include node $V_3$ include: GAC (from nodes $V_0$, $V_2$, and $V_3$); ACG (from nodes $V_2$ and $V_3$); and CGT, GTT, and TTT (from node $V_3$ only.) The sequences GAC and ACG include non-visited nodes, and thus may be considered for comparison with the sequence read 610. However, once there is an attempt to compare the sequence read 610 to CGT, the comparison would be against a subsequence generated entirely from a visited node. (This comparison would have previously been performed during evaluation of the search path $\{V_0, V_1, V_3, V_5\}$.) Accordingly, the graph traversal module 302 immediately backtracks, removing node $V_0$ from the search path and attempting to extend again from node $V_2$. Node $V_2$ has no unfollowed child nodes, so backtracking results in a search path containing only node $V_0$. Node $V_0$ has no unfollowed child nodes, so it is removed. As shown in FIG. 8B, the graph traversal is complete.

It should be noted that the above-described exemplary applications of systems and methods according to the disclosure (e.g., as shown in FIGS. 6A-E and 8A-B) illustrate the traversal and comparison of a sequence read that is only 3 base pairs in length. However, in typical applications, a sequence read will have a longer length (e.g., 50-500 bp). In such cases, comparisons of the sequence read to the graph may often span multiple nodes. For example, consider a 7 base pair sequence. When the search path is $\{V_0, V_2, V_3\}$ as shown in FIG. 8A, we may further add nodes $V_5$, and then after backtracking, $V_4$, $V_5$ to the search path 615 to evaluate node $V_2$ ("A") in combination with the sequences generated by those paths. However, once we have a subsequence that considers only the nucleotide sequence from nodes $V_3$, $V_5$ or $V_3$, $V_4$, $V_5$ (i.e., the subsequence that is generated begins from $V_3$, a visited node), the search is modified by removing the last node from the search path (here, $V_5$) immediately before attempting to perform any further comparisons with sequences generated by that search path. The next attempt to extend begins from node $V_3$. In other words, the search is modified by immediately backtracking when a sequence comparison begins with a sequence generated only from visited nodes. In this way, methods according to the disclosure are able to align a sequence read to a graph reference across multiple paths, yet efficiently remove previously considered paths from testing.

By removing redundant paths from consideration (e.g., by backtracking early), systems and methods according to the disclosure result in a substantial improvement in the speed and efficiency of sequence read alignment to a graph reference. In particular, fewer substrings are generated for comparison with a sequence read. Moreover, because only redundant paths and corresponding subsequences are removed from consideration, there is no corresponding decrease in the accuracy of alignment.

Sequence Comparison

As noted above, as the graph is traversed, the sequence read 610 is compared to sequences generated by concatenating the nucleotide sequences associated with each of the nodes in the search path 615. This can be performed in a variety of ways. As shown in FIG. 3, the graph alignment engine 114 further comprises the sequence comparison module 304. The sequence comparison module 304 is configured to compare a sequence read 112 with a corresponding sequence generated from the graph reference 116, such as a concatenated sequence or subsequence generated from a set of nodes according to a search path produced by the graph traversal module 302. More specifically, in this embodiment, the sequence comparison module 304 is considering the k-differences problem, a version of an approximate string matching problem.

Given two strings and an integer k, the k-differences problem attempts to find all approximate occurrences of a string within a larger text according to at most k editing operations (e.g., mismatches, insertions, or deletions). For example, consider a sequence read P having a length m and consisting of an ordered set of nucleotides p, i.e., $P=p_1, p_2, \ldots p_m$. A reference sequence T has a length n and similarly consists of an ordered set of nucleotides t, i.e., $T=t_1, t_2, \ldots t_m$. Both p and t are built over a finite set of characters of an alphabet size denoted by $|\Sigma|$, wherein $\Sigma \in \{A, C, G, T\}$. A candidate alignment is a set of positions on T to which N potentially matches. A naïve, or brute force, method of identifying a set of candidate alignments involves directly comparing the first m characters of the reference sequence T with the short read P. After a match or a mismatch determination, the sequence read is shifted to the next position for another comparison. This approach runs in O(mn) time. If allowing for a certain number of mismatches k between the short read and the genome, the time increases to O(mnk).

Alignment speed can be improved by reducing the number of required comparisons, e.g., by using a string matching algorithm that reduces the number of required comparisons between a sequence read and a reference sequence. As noted above, in an alignment, a sequence read P is aligned with the left-most portion of a reference sequence T, creating a window of length n. After a match or mismatch determination, the window is shifted to the right. Certain string matching algorithms, such as the Boyer-Moore and Tarhio-Ukkonen algorithms, increase efficiency by shifting the window farther to the right than a single character, i.e., by skipping a certain number of comparisons which would not result in an aligned position. In particular, these string matching algorithms process the sequence read, or pattern, itself in order to create a "shift table" that indicates how many comparisons can safely be skipped depending on the mapping of short read at the current position. The number of comparisons that can safely be skipped can be referred to as a "shift value." The shift value greatly increases the speed of pattern matching by skipping comparisons that would result in a mismatch determination.

Furthermore, when applied to a graph reference, a shift value may indicate a shift that extends beyond a nearby dense or complex region of the graph that includes many variations. Each of these variations would typically be evaluated in combination with one another, resulting in excessive computation. Tarhio-Ukkonen and similar algorithms thus have the potential to avoid a large number of unnecessary comparisons, resulting in a significant improvement in the speed of graph alignment.

To create a shift table, many algorithms operate in two phases: a pre-processing phase and a search phase. The pre-processing phase typically processes the pattern itself to generate information that can aid the search phase by providing a table of shift values after each comparison. Improvement in efficiency of a search can be achieved by altering the order in which the characters are compared at each attempt, and by choosing a shift value that permits the skipping of a predefined number of characters in the text after each attempt. The search phase then uses this information to ignore certain character comparisons, reducing the total number of comparisons and thus the overall execution time.

The Boyer-Moore algorithm is one of the most efficient. Boyer-Moore preprocesses a pattern to create two tables: a Boyer-Moore bad character (bmBc) table and a Boyer-Moore good-suffix (bmGs) table. For each character in Σ, the bad character table stores a shift value based on the occurrence of the character in the pattern, or short read. The good-suffix table stores the matching shift value for each character in the read. The maximum of the shift value in either table is considered after each comparison during search, which is then used to advance the window. Boyer-Moore does not allow any mismatches between the read and reference sequence, and thus is a perfect-match search algorithm. More information on the Boyer-Moore algorithm can be found in Boyer, R. S., Moore, J. S., "A Fast String Searching Algorithm", Comm. ACM 20(10), 762-772.

The Boyer-Moore algorithm serves as the basis for several pattern matching algorithms that can be used for sequence alignment. One variation of Boyer-Moore is the Horspool algorithm (1980). Horspool simplifies Boyer-Moore by recognizing that the bad-character shift of the right-most character of the window can be sufficient to compute the value of the shift. These shift values are then determined in the pre-processing stage for all of the characters in the alphabet Σ. Horspool is more efficient in practical situations when the alphabet size is large and the length of the pattern is small. Like Boyer-Moore, the Horspool algorithm is a perfect-match search algorithm. More information on the Horspool algorithm can be found in Horspool, R. N., "Practical Fast Searching in Strings", Software-Practice & Experience, 10, 501-506.

Another variation of Boyer-Moore that allows for a certain number of mismatches is the Tarhio-Ukkonen algorithm. During the pre-processing phase, Tarhio-Ukkonen calculates shift values for every character that take into account a desired allowable number of mismatches, k. Tarhio-Ukkonen is able to identify matches in expected time $$O\left(kn\left(\frac{1}{m-k} + \frac{k}{c}\right)\right),$$

where c is the size of the alphabet Σ. The use of approximation in pattern matching algorithms such as Tarhio-Ukkonen is particularly useful for next generation sequencing applications due to the inherent noise present in sequence reads generated by most next generation sequencing technologies. Furthermore, because the primary goal of sequence analysis is to identify unknown variations that may be present in a sample, approximate pattern matching algorithms help to identify novel polymorphisms in sequence data. Accordingly, allowing for k mismatches allows for sensitivity to both errors and unknown variations that may be present in a sample. In contrast, the Boyer-Moore and Horspool algorithms would reject such reads if there were any differences between the read and the reference. More information on the Tarhio-Ukknonen algorithm can be found in Tarhio, J., Ukkonen, E., "Approximate Boyer-Moore String Matching", SIAM J. Comput., 22, 243-260.

When used for next generation sequence alignment, the Boyer-Moore family of string matching algorithms can be used as a fast local alignment tool. However, these algorithms do not handle insertions and deletions as well as dynamic programming approaches (such as Smith-Waterman and Needleman-Wunsch), and thus have not been favored approaches for traditional sequence read alignment. However, the inventors have recognized that such string matching algorithms are ideally suited for aligning sequence reads to a graph reference. In particular, the string matching algorithm does not need to consider a large number of mismatches or attempt to allow for a number of gaps, because variations are already accounted for as alternate paths through the graph reference. Accordingly, such algorithms can quickly and efficiently scan through a graph reference to identify approximate matches of a sequence read. Accordingly, the sequence comparison module 304 of FIG. 3 can utilize such string matching algorithms to efficiently compare a sequence read 112 to a search path generated according to a traversal of the graph reference 116.

While Tarhio-Ukkonen and other k-mismatch pattern matching algorithms are ideally suited for a graph reference, in certain cases such algorithms may not generate an ideal (or any) alignment for a given sequence read. This may occur in situations where a sequence read has several errors, or if the sequence read includes complicated mutational events such as insertions or deletions. For example, if the pattern matching algorithm is set to allow only 0 or 1 mismatches from the reference (which results in an extremely fast alignment), a substantial number of reads may not be aligned. Accordingly, in some embodiments, if no acceptable results from a pattern matching algorithm are generated, then a graph alignment engine according to the disclosure may attempt to align the read to the graph reference using a second algorithm, such as a Smith-Waterman algorithm or Needleman-Wunsch algorithm, in order to "rescue" the sequence read. In further embodiments, the second algorithm may be a graph-aware Smith-Waterman algorithm, such as the algorithm disclosed in U.S. Patent Publication 2015/0057946. In any of these embodiments, any loss in sensitivity by applying strict or semi-strict pattern matching may be resolved by applying the second algorithm in certain cases.

Scoring Potential Aligned Positions

The graph traversal module 302 and sequence comparison module 304 interact by "walking" a sequence read along possible positions within the graph reference, and then comparing the sequence read with sequences generated from those positions. Use of a pattern matching algorithm such as Tarhio-Ukkonen further accelerates sequence read alignment to a graph in regions that are dense with variations by outputting an amount by which to shift she sequence read forward at each step. Potential matches may then be scored, and a best-fit position may be selected as the aligned position of the sequence read.

The scoring module 306 is configured to score alignments, or approximate matching positions, of a sequence read 112 against the graph reference 116 in order to identify the most likely position of that sequence read, i.e., the most likely position from which that sequence read originated. In one example, the scoring module 306 may receive a plurality of aligned positions from the sequence comparison module 304 for a given sequence read 112, and determine a best position to report as the aligned position for that sequence read 112. For example, if the sequence comparison module 304 is using a Smith-Waterman algorithm, the scoring module 306 may perform a backtracking step (not to be confused with the graph traversal backtracking described herein) in a set of matrices in order to identify the optimal aligned position of a sequence read. Alternately, if the sequence comparison module 304 is using a pattern matching algorithm (e.g., Tarhio-Ukkonen), the scoring module 306 may consider which positions on the graph reference have a minimum number of differences from the sequence read.

As sequence reads tend to be relatively short sequences (e.g., 50-500 bp), often they may ambiguously align (or "map") equally well to multiple regions of a reference sequence. This often occurs in large mammalian genomes, which have many large repetitive elements, such as tandem repeats, interspersed repeats, and segmental duplications. Accordingly, the scoring module 306 may consider various criteria when resolving the best alignment position for a sequence read. In one example, ambiguity can be resolved by determining a mapping quality (MQ) score, which measures the confidence that a sequence read is generated from the position it is aligned to in the reference genome by the alignment algorithm. For example, an alignment algorithm may estimate mapping quality by considering the per-base quality scores at each position of a sequence read, allowing the algorithm to infer a most likely mapped position. (More information on mapping quality can be found in Heng Li, Jue Ruan, and Richard Durbin, Mapping Short DNA Sequencing Reads and Calling Variants using Mapping Quality Scores, Genome Res. 2008 November; 18(11): 1851-1858.) Accordingly, the result of a sequence alignment will typically comprise a mapped position for each read, a mapping quality, and an alignment indicator describing properties of the mapped position (which may include base mismatches and the presence of gaps).

Alignment By k-mer Match Extension

The inventors have appreciated that complex regions of a graph reference may result in a significant decrease in speed of alignment. This is due to an increase in combinatorial complexity that quickly increases the number of possible comparisons to a point where improvements in efficiency are lost. In other words, the expected time for the graph alignment engine 114 to traverse, compare, and score aligned positions of a sequence read against a graph reference may be multiplied by the number of possible paths.

The inventors have further recognized that this problem can be compounded by the length of a sequence read. For example, sequence reads may span several nodes in a given path, requiring the consideration of various combinations of those nodes. The improved depth-first search techniques as described above result in a significant improvement in that fewer paths are considered. However, for longer sequence reads and dense regions of the graph, no increase in speed may be seen. This is because during alignment, the sequence read may often be positioned against several visited nodes; however, as long as one node in the current comparison is not marked as visited, those combinations will still be considered.

Accordingly, the inventors have appreciated that short sequences, such as between 5 and 30 base pairs, can be quickly aligned to a graph reference as they will require fewer considerations of multiple combinations of nodes. The increase in efficiency results from the understanding that there are fewer sequences of short length, e.g., 5-30 base pairs, generated by a depth-first search from a dense graph then there are when aligning sequences of longer length, e.g., 50-500 base pairs. In particular, the time taken to identify matches for short length sequences increases linearly rather than exponentially with graph density, particularly if most variations within the graph are more than the sequence read length away from each other.

For example, the table below illustrates the number of corresponding sequences generated by traversing a graph reference for a variety of sequence read lengths. For a 150 base pair sequence read, 888,403 sequences were generated for comparison. Using a modified depth-first search as described by the disclosure, the percent time decrease was 8% (i.e., compared to a traditional depth-first search). Halving the read length to 75 base pairs resulted in an 88.5% decrease in the number of sequences generated for comparison, and a corresponding decrease in time of 68% compared to an unmodified depth-first search. Reducing the read length further still resulted in only 2,394 sequences found, with a decrease in the time required for alignment of 97.5%.

| Sequence Read Length | Graph Sequences Generated | % Time Decrease |
| --- | --- | --- |
| 150 | 888,403 | 8% |
| 75 | 101,980 | 68% |
| 25 | 2,394 | 97.5% |

Accordingly, the inventors have recognized that the search space of a graph reference can be reduced by aligning relatively short k-mers, or substrings, of a sequence read to a graph reference. In these embodiments, the aligned positions of the k-mers may be reported by the scoring module 306 to the match extension module 308. The match extension module 308 can then attempt to "extend" these short matches, e.g., by considering additional bases beyond the matched position. Certain positions may have immediate mismatches and not extend, whereas others may extend to the full length of the sequence read. These latter cases may then be reported as the final aligned positions of the sequence read 112 by the scoring module 306. This results in an extremely fast method of sequence read alignment to a graph reference, and in particular, complex graph references or regions of graph references with many variations.

Figure 9A:
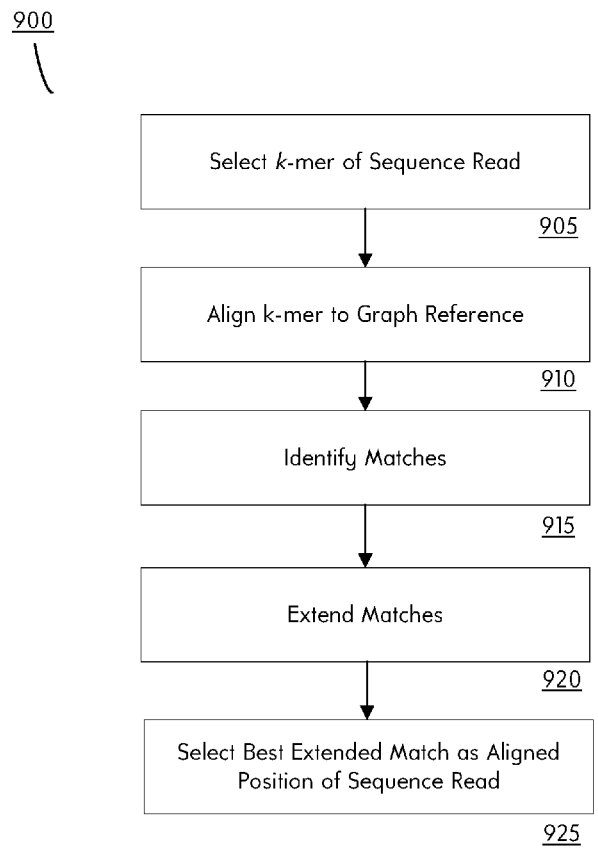
FIG. 9A is a flow diagram illustrating a method of aligning a sequence read to a graph.

FIG. 9 depicts an illustrative method 900 of aligning a sequence read to a graph reference according to an embodiment of the disclosure. The method 900 can begin at act 905 by selecting a k-mer of the sequence read. The k-mer can comprise a fixed length, e.g., 5-30 base pairs, or alternately may be a percentage, e.g., 5-30%, of a sequence read. In this embodiment, the k-mer selected may begin from the first position of the sequence read. However, in other embodiments, the k-mer may begin from other portions of the sequence read. This may be helpful in situations in which the first position of the sequence read may have segments known to be repetitive in the graph reference, for example.

The selected k-mer is then aligned to a graph reference at act 910. Alignment to a graph reference can proceed using any form of sequence read alignment to a graph reference, e.g. the methods 400, 500, 700, 750, various other embodiments of the disclosure, and combinations thereof. Positions at which the k-mer aligns to the graph reference, or "matches," are noted at act 915. These positions may be those at which the k-mer has a minimum of differences from the graph reference. Next, the matches are extended at act 920 by considering whether the additional bases of the sequence read beyond the k-mer also result in a minimum of differences from the graph reference. This can be performed sequentially, e.g., by considering each additional base, and then removing potential matches from consideration if the number of mismatching base pairs or gaps at that position exceed a threshold level (e.g., 1-15 mismatches). This could also be performed by simply generating the entire sequence at this position and performing a comparison with the full sequence read, e.g. by using the Smith-Waterman algorithm, for example. Finally, the best match (or matches) may be reported as the aligned position of the sequence read at act 925.

While fewer sequences may be generated by a graph traversal using a k-mer of the sequence read, the number of reported matches, or aligned positions, may increase. This is because there may be a single best-fit position for an entire sequence read in the graph reference, but there may be many best-fit positions for a k-mer of that sequence read. However, even when many best-fit positions are found, the subsequent extension step afterwards is fast and weeds out false matches. Accordingly, the value of k selected may have a lower bound of about 5-6 base pairs depending on the density and structure of the graph. In certain graph references, a value as low as 4 base pairs may also be sufficient. However, k-mers shorter than 4 base pairs may result in an excessive number of matches to consider, and thus reduce the benefits of a faster initial search.

Further, it should be noted that a k-mer match extension as described herein is particularly useful for "long read" next-generation sequencing technologies, such as PacBio® Single Molecule, Real-Time (SMRT) Sequencing, which can generate sequence reads that range from 10,000 to 60,000 base pairs. Aligning short k-mers from these sequences will quickly find a set of candidate regions for evaluation, rather than attempting to extend the full sequence through all combinations of nodes. In such embodiments, one may choose to align longer k-mers of the sequence read, e.g., 100 bp, 1000 bp, or more.

Figure 9B:
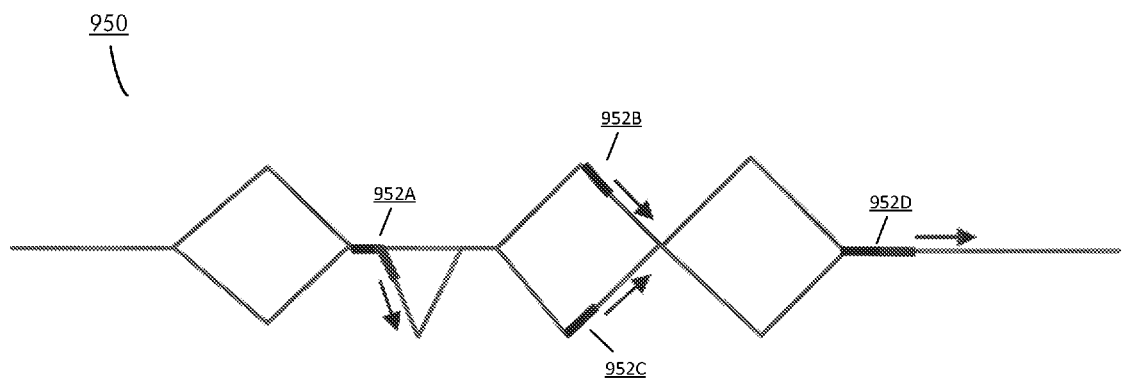
FIG. 9B is an illustrative diagram of a graph-based reference sequence construct, in accordance with some embodiments of the technology described herein.

FIG. 9B depicts an exemplary graph reference 950. As shown in FIG. 9B, several matches 952A, 952B, 952C, 952D of k-mers of a sequence read have been aligned to the graph reference 950. These k-mers may then be extended, e.g., by act 920 of the method 900, in order to identify a best-fit aligned position of the sequence read.

It should be noted that there are techniques in the art exist to reduce the search space of a reference sequence by performing a coarse, i.e., "global" search to initially identify a set of candidate locations, and subsequently performing a fine, i.e., "local" search to then refine those results. However, these techniques are typically hash-based, and search for positions in a sequence read having hash values that match hash values of positions in the reference. This is computationally expensive and often requires an initial pre-processing of the reference sequence. In contrast, a k-mer match finding and extension as described by the present disclosure is fundamentally different in that the k-mer matches are initially identified by a graph traversal, and in particular, the k-mer matches may be found using exemplary embodiments of graph traversal as described herein. These methods are faster than traditional hash-based techniques, particularly when applied to graph references dense with variation.

In some embodiments, k-mer match extension may be selectively applied, i.e., to regions of a graph having an excessive number of variants, or regions of a graph having a large number of variants close to one another (e.g., within the length of the sequence read to be aligned).

Further, it should be noted that various combinations of embodiments described by the disclosure may be combined or omitted in various ways. For example, one embodiment comprises a depth-first search of a graph reference, e.g., one or both of the methods 400, 500 of FIGS. 4-5. Another embodiment comprises a modified depth-first search of a graph reference by removing redundant paths from consideration, such as the method 700, 750 of FIGS. 7A-B. Another embodiment comprises performing a k-mer match extension of a graph reference, such as the method 900 of FIG. 9. These embodiments may be combined in various ways, as the disclosure is not intended to be limiting in this respect.

Output Information

As shown in FIG. 3, once the set of sequence reads 112 have been aligned to the graph reference 116, the sequence reads and their corresponding aligned positions are then reported, e.g. as a set of sequence read alignments 312 as shown in FIG. 3. These may be reported in SAM/BAM format, graph-based formats, tabular formats, and the like. The alignments may include indications of each alignment, such as an alignment indicator (e.g., a Compact Idiosyncratic Gapped Alignment Report, or CIGAR string). Additionally, auxiliary output information 314 may also be generated, which can comprise log files, various statistics associated with the alignment, and other information that can describe properties of the sequence reads, the graph reference, and the alignment itself.

Exemplary Results for k-mer Match Extension

Figure 10A:
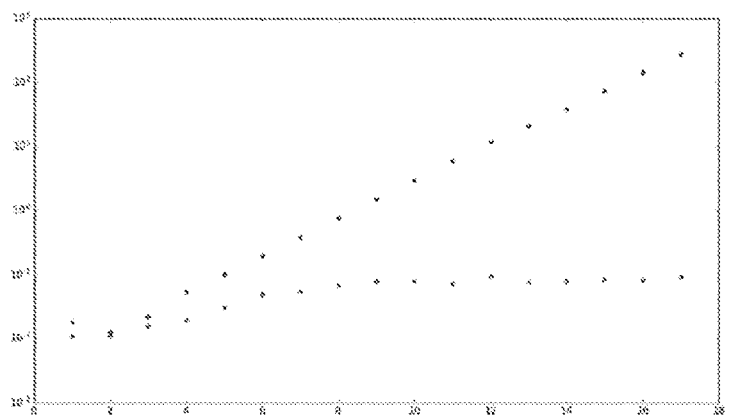
FIGS. 10A-C and 11A-B depict charts illustrating speed and efficiency improvements of sequence read alignment in accordance with some embodiments of the technology described herein.
Figure 10B:
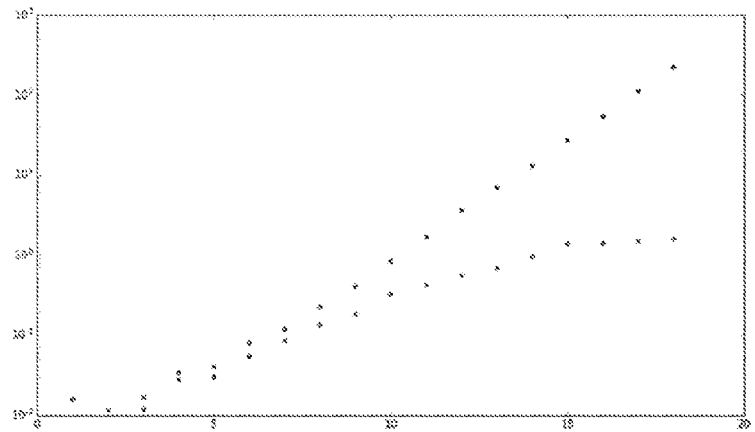
Figure 10C:
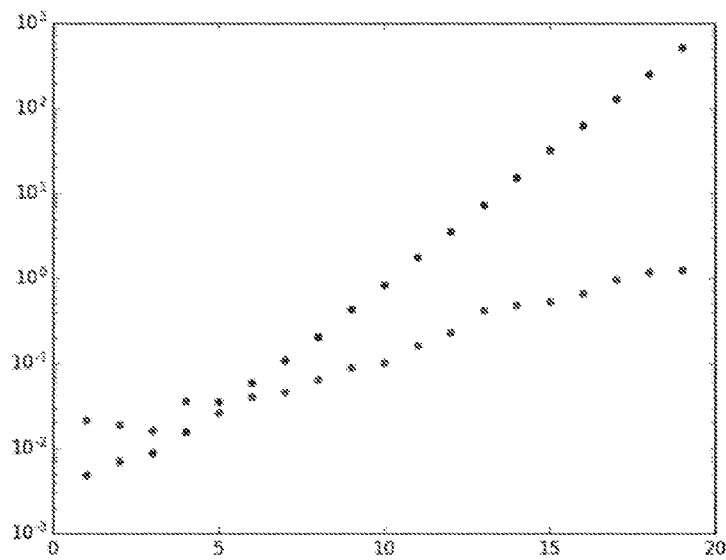

FIGS. 10A-C are charts comparing the run times of a an embodiment of a modified depth-first search algorithm that marks nodes as "visited" with a corresponding algorithm that applies an embodiment of a k-mer match extension technique. In FIGS. 10A-C, the X-axis indicates the complexity of the graph, here expressed as the number of variations included in the graph, and the Y-axis indicates run time in seconds. As shown in FIGS. 10A-C, despite the improvements previously shown for the modified depth first search, as the number of variations increase, the runtime of scales exponentially (note that the Y-axis is in logarithmic scale). In contrast, a modified depth-first search algorithm k-mer match extension holds steady in most cases, or converges to a maximum. This is because the number of additional paths considered for a sequence read by the modified depth-first search using k-mer match extension is limited by the shorter length of the k-mer. Thus, methods according to the disclosure can result in linear or near-linear time.

Figure 11A:
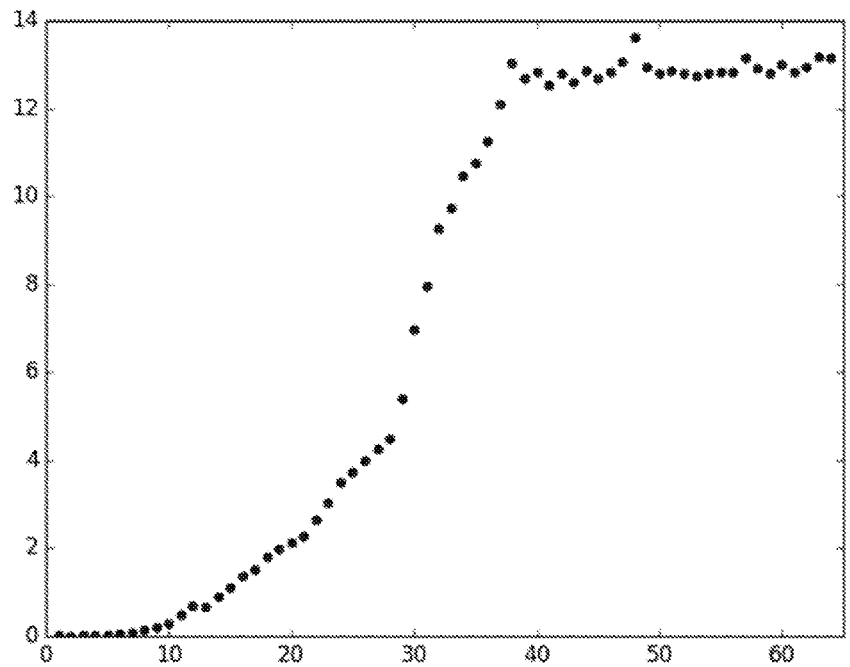
Figure 11B:
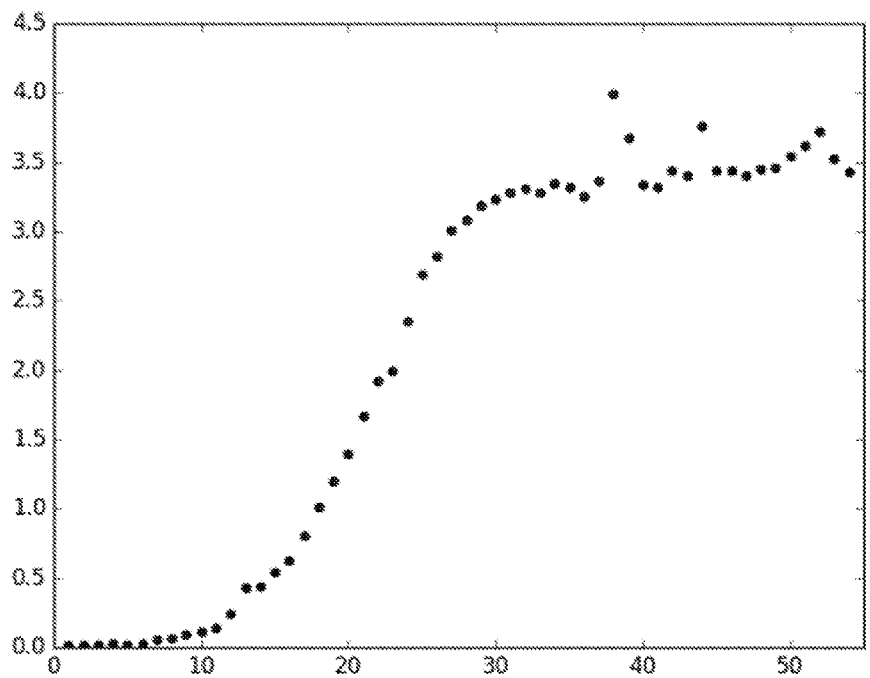

FIGS. 11A-B are charts further illustrating the run times of algorithms according to the disclosure. In particular, the charts depict the run time of a modified depth-first search algorithm using k-mer match extension, but here the Y-axis is in linear scale. Similar to the charts of FIGS. 10A-C, the run time increases as the number of variations increase, but then plateaus. Similarly, the additional variations beyond the length of the k-mer are not being considered by virtue of the reduction in search space.

Additional Definitions

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements.

This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A system for aligning a sequence read to a graph reference, the system comprising:
   at least one computer hardware processor; and
   at least one non-transitory computer-readable storage medium storing: a graph reference, the graph reference comprising a plurality of nodes connected by a plurality of edges, at least one node of the plurality of nodes having an associated nucleotide sequence; a plurality of sequence reads; and processor-executable instructions that, when executed by the at least one computer hardware processor, cause the at least one computer hardware processor to perform:
   selecting a first node of the plurality of nodes;
   identifying a first path by traversing the graph reference, the first path starting from the first node and comprising at least one child node of the first node;
   comparing at least one first nucleotide sequence generated from the first path with the sequence read, wherein the at least one first nucleotide sequence is generated at least in part by concatenating associated nucleotide sequences from nodes in the first path into the at least one first nucleotide sequence;
   identifying a second path by traversing the graph reference, the second path starting from the first node and comprising at least one node not considered by the first path;
   comparing at least one second nucleotide sequence generated from the second path with the sequence read, the comparing comprising determining whether the at least one second nucleotide sequence generated from the second path was previously generated by the first path, and removing one or more nodes from the identified second path based on the determination;
   determining a best-fit position of the sequence read on the graph reference; and
   reporting the best-fit position of the sequence read as the aligned position of the sequence read on the graph reference.

2. The system of claim 1, wherein traversing the graph reference comprises performing a depth-first search.

3. The system of claim 1, wherein a path comprises one or more nodes.

4. The system of claim 1, wherein identifying a first path by traversing the graph reference comprises following outgoing edges of successive nodes until reaching a last node having no outgoing edges.

5. The system of claim 4, wherein identifying a second path by traversing the graph reference comprises backtracking from the last node having no outgoing edges.

6. The system of claim 5, wherein backtracking from the last node having no outgoing edges further comprises identifying a node having a previously unfollowed outgoing edge, following the previously unfollowed outgoing edge, and following outgoing edges of successive nodes until reaching a last node having no outgoing edges.

7. The system of claim 1, wherein each node further comprises a followed indicator that indicates which of its outgoing directed edges have been traversed, and traversing the graph reference further comprises updating the followed indicator when following an outgoing edge from that node.

8. The system of claim 7, wherein each node further comprises a visited indicator that indicates whether all of its outgoing directed edges have been traversed, wherein traversing the graph reference further comprises:
  determining whether a node's followed indicator indicates that all of its outgoing directed edges have been traversed;
  updating the node's visited indicator to indicate that all of the outgoing directed edges have been traversed;
  resetting the node's followed indicator to indicate that all of the outgoing directed edges have not been traversed; and
  backtracking from the node.

9. The system of claim 8, wherein comparing at least one second nucleotide sequence generated from the second path with the sequence read further comprises considering whether the at least one second nucleotide sequence is generated entirely from nodes having visited indicators that indicate all of the outgoing directed edges of those nodes have been traversed.

10. The system of claim 1, wherein comparing at least one first nucleotide sequence generated from the first path with the sequence read further comprises:
  identifying a first set of substrings of the at least one first nucleotide sequence; and
  comparing the first set of substrings to the sequence read.

11. The system of claim 10, wherein comparing at least one second nucleotide sequence generated from the second path with the sequence read comprises:
  concatenating nucleotide sequences associated with the nodes in the second path into a second concatenated nucleotide sequence;
  identifying a second set of substrings of the second concatenated nucleotide sequence;
  comparing each substring of the second set of substrings to the sequence read if and only if a substring is not within the first set of substrings.

12. The system of claim 11, wherein comparing each substring of the second set of substrings to the sequence read if and only if a substring is not within the first set of substrings comprises considering whether a substring is generated from at least one node that was not present in the first path.

13. The system of claim 12, wherein each node further comprises a visited indicator that indicates whether all of that node's outgoing directed edges have been traversed, and comparing each substring of the second set of substrings further comprises:
  determining whether each of the nodes associated with a substring have visited indicators that indicate all of the outgoing directed edges of those nodes have been traversed;
  if each of the nodes associated with the substring have visited indicators that indicate all of the outgoing directed edges of those nodes have been traversed, removing the most recently added node from the second path and considering whether any remaining nodes in the second path have an unfollowed outgoing edge; and
  if any of the nodes associated with the substring have visited indicators that indicate all of the outgoing directed edges of those nodes have not been traversed, comparing the substring with the sequence read.

14. The system of claim 13, wherein comparing the substring with the sequence read further comprises generating the substring from those nodes.

15. The system of claim 1, wherein identifying a second path by traversing the graph reference comprises:
  identifying a quantity of nodes within the graph reference;
  traversing a portion of the graph reference; and
  modifying traversal of the graph in response to a determination that a region of the graph has been previously considered by the first path.

16. The system of claim 1, wherein identifying a first path by traversing the graph reference comprises:
  considering whether the first node has an unfollowed child node;
  if the first node has an unfollowed child node, adding the unfollowed child node to the first path.

17. The system of claim 1, wherein the sequence read comprises a k-mer of the sequence read, wherein comparing nucleotide sequences generated from a path with the sequence read comprises comparing a k-mer of the sequence read with the nucleotide sequences.

18. The system of claim 17, wherein the k-mer begins from the first base of the sequence read.

19. The system of claim 17, wherein the length of the k-mer is between 5 and 30 base pairs.

20. The system of claim 17, further comprising determining one or more best-fit positions of the k-mer of the sequence read.

21. The system of claim 20, further comprising determining a best-fit position of the sequence read by considering additional nucleotides adjacent to the best-fit positions of the kmer of the sequence read.

22. The system of claim 1, wherein determining a best-fit position of the sequence read on the graph reference further comprises:
  aligning the sequence read to the graph reference using a second alignment algorithm.

23. The system of claim 22, wherein the second alignment algorithm is selected from the group consisting of: the Smith-Waterman algorithm and a graph-aware Smith-Waterman algorithm.

* * * * *